US012173034B2

(12) United States Patent
Fujinaga et al.

(10) Patent No.: US 12,173,034 B2
(45) Date of Patent: Dec. 24, 2024

(54) HEMAGGLUTININ COMPLEX PROTEIN AND APPLICATION THEREOF

(71) Applicant: OSAKA UNIVERSITY, Osaka (JP)

(72) Inventors: Yukako Fujinaga, Kanazawa (JP); Sho Amatsu, Kanazawa (JP); Masahiro Kinooka, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 1148 days.

(21) Appl. No.: 16/766,596

(22) PCT Filed: Nov. 22, 2018

(86) PCT No.: PCT/JP2018/043249
§ 371 (c)(1),
(2) Date: May 22, 2020

(87) PCT Pub. No.: WO2019/103111
PCT Pub. Date: May 31, 2019

(65) Prior Publication Data
US 2021/0122790 A1    Apr. 29, 2021

(30) Foreign Application Priority Data

Nov. 24, 2017   (JP) ................................ 2017-226370

(51) Int. Cl.
*C07K 14/33*   (2006.01)
*C12N 15/85*   (2006.01)

(52) U.S. Cl.
CPC .............. *C07K 14/33* (2013.01); *C12N 15/85* (2013.01)

(58) Field of Classification Search
CPC ..... C07K 14/33; C07K 2319/00; C12N 15/85
See application file for complete search history.

(56) References Cited

U.S. PATENT DOCUMENTS

| | | | | |
|---|---|---|---|---|
| 7,514,088 B2 * | 4/2009 | Steward | ............ | A61K 38/4886 424/234.1 |
| 11,230,701 B2 * | 1/2022 | Kinooka | ............ | C12N 5/0696 |
| 2014/0235836 A1 * | 8/2014 | Song | .................... | C07K 14/005 530/396 |
| 2015/0329831 A1 | 11/2015 | Kinooka et al. | | |
| 2017/0130206 A1 | 5/2017 | Kinooka et al. | | |

FOREIGN PATENT DOCUMENTS

| | | | | |
|---|---|---|---|---|
| EP | 3 153 175 A1 | 4/2017 | | |
| JP | 2 953 670 | * 12/2016 | ............ | C07K 19/00 |
| WO | 2014/104207 A1 | 7/2014 | | |
| WO | 2015/199243 A1 | 12/2015 | | |

OTHER PUBLICATIONS

Fujinaga et al., Interaction of Botulinum Toxin with the Epithelial Barrier. J. Biomed. Biotechnol., 2010, Article ID 974943: 1-9. (Year: 2010).*
Juan Jae., MSc., Hemagglutinin-based antigen designs expressed in the methylotrophic yeast *Pichia pastoris*. Thesis, Laurentian Univ., Ontario, Canada, 2016, pp. 1-169. (Year: 2016).*
Sakaguchi et al., Genomics of Clostridium botulinum group III strains. Res. Microbiol., 2015, vol. 166: 318-325. (Year: 2015).*
Sugawara et al., The botulinum toxin complex meets E-cadherin on the way to its destination. Cell Adhesion & Migration, 2011, vol. 5:1: 34-36 (Year: 2011).*
Kwangkook Lee et al., "Structure of a Bimodular Botulinum Neurotoxin Complex Provides Insights into its Oral Toxicity", PLOS/Pathogens, Oct. 2013, pp. 1-13, vol. 9, Issue 10, Article e1003690.
International Search Report for PCT/JP2018/043249, dated Feb. 5, 2019.
Sugawara et al., "Functional Dissection of the *Clostridium botulinum* Type B Hemagglutinin Complex: Identification of the Carbohydrate and E-Cadherin Binding Sites", PLOS ONE, Oct. 2014, vol. 9, Issue 10, e111170 (9 pages).
Supplementary European Search Report dated Jul. 30, 2021 in EP Application No. 18 88 0123.
Jin et al., "Disruption of the epithelial barrier by botulinum haemagglutinin (HA) proteins—differences in cell tropism and the mechanism of action between HA proteins of types A or B, and HA proteins of type C", Microbiology, vol. 155, pp. 35-45, 2009 (11 pages total).
Matsumura et al., "The HA proteins of botulinum toxin disrupt intestinal epithelial intercellular junctions to increase toxin absorption", Cellular Microbiology, vol. 10, No. 2, pp. 355-364, 2008 (10 pages total).
Sugawara et al., "Botulinum hemagglutinin disrupts the intercellular epithelial barrier by directly binding E-cadherin", J. Cell. Biol., vol. 189, No. 4, pp. 691-700, 2010 (10 pages total).
Amatsu et al., "Crystal Structure of Clostridium botulinum Whole Hemagglutinin Reveals a Huge Triskelion-shaped Molecular Complex", J. Biol. Chem., vol. 288, No. 49, pp. 35617-35625, Dec. 6, 2013 (10 pages total).
Lee et al., "Molecular basis for disruption of E-cadherin adhesion by botulinum neurotoxin A complex", Science, vol. 344, No. 6190, pp. 1405-1410, Jun. 20, 2014 (11 pages total).

* cited by examiner

*Primary Examiner* — Ganapathirama Raghu
(74) *Attorney, Agent, or Firm* — Sughrue Mion, PLLC

(57) ABSTRACT

The present invention provides a miniaturized hemagglutinin complex protein having function inhibitory activity against E-cadherin, wherein
(a) all or a part of at least HA1 subcomponent, and/or a part of HA3 subcomponent are/is deleted,
(b) regions in HA2 and HA3 subcomponents that contribute to binding with E-cadherin are present, and
(c) the HA3 subcomponent is derived from *Clostridium botulinum* type A or type B, and an E-cadherin function inhibitor containing the hemagglutinin complex protein.

8 Claims, 12 Drawing Sheets

Specification includes a Sequence Listing.

Amino acid sequence of nano-HA (linked-mini(2+3)/CB-LD-YFDY)

```
       380         390         400         410         420         430
MAS

HEMAGGLUTININ COMPLEX PROTEIN AND APPLICATION THEREOF

CROSS REFERENCE TO RELATED APPLICATIONS

This application is a National Stage of International Application No. PCT/JP2018/043249 filed Nov. 22, 2018, claiming priority based on Japanese Patent Application No. 2017-226370 filed Nov. 24, 2017.

TECHNICAL FIELD

The present invention relates to a novel miniaturized hemagglutinin complex protein maintaining cadherin function inhibitory activity, and use thereof.

BACKGROUND ART

When cells deviated from an undifferentiated state (hereinafter to be also referred to as "deviated cells") are accidentally developed in the process of maintenance or amplification culture of pluripotent stem cells such as induced pluripotent stem cells (hereinafter to be also referred to as "iPS cells") and the like, the conversion of undifferentiated cells to deviated cells is further induced, the proliferation of undifferentiated cells is suppressed, and the undifferentiated state becomes difficult to maintain. Therefore, it is necessary to remove the colonies containing deviated cells; however, this work is performed by a pipetting operation under a microscope during subculturing, and involves complicated and skill-requiring procedures. While an automated device for the work has been developed, it has not yet been fully automated or spread, and a simple method for maintaining undifferentiated pluripotent stem cells (removal and/or suppression of development of deviated cells) has been demanded.

The present inventors have found that hemagglutinin, a component of the botulinum neurotoxin complex (hereinafter to be also referred to as "HA") specifically binds to the cell adhesion factor, E-cadherin, and inhibits its function, thereby disrupting the intercellular barrier function (non-patent documents 1-3). A method using this cadherin function inhibitory activity of HA for removing the deviated cells generated in the colonies of pluripotent stem cells and maintaining the undifferentiated state of the pluripotent stem cells has already been reported (patent documents 1 and 2).

HA is constituted of three different subcomponents of HA1 (also called HA33), HA2 (also called HA17) and HA3 (also called HA70) (constituted of HA1:HA2:HA3=6:3:3 stoichiometry), and has a triskelion-like conformation in which three arms composed of HA1 (dimer) and HA2 are bound to HA3 (non-patent document 4). To recombinantly produce the whole HA complex (FL-HA; see FIG. 1), therefore, a step of expressing and purifying respective subunit proteins, mixing and incubating the three to form a 12-mer having the above-mentioned conformation, and further purifying same is required. Thus practicalization involves problems in terms of time, labor, cost, and the like.

If HA complex can be miniaturized while maintaining the cadherin function inhibitory activity, the production step can be simplified and an HA complex easy to handle can be provided. Thus, it can be greatly expected as a tool for maintaining undifferentiated pluripotent stem cells. However, the research group of Jin et al. has reported that a miniaturized HA complex constituted of HA1 dimer, HA2 and HA3 fragments (consisting of Pro at position 378 to Asn at position 626) (mini-HA; see FIG. 1) binds to E-cadherin but does not have barrier disruption activity, and considers that HA needs to be polyvalent to achieve barrier disruption activity (non-patent documents 5 and 6).

DOCUMENT LIST

Patent Documents patent document 1: WO 2014/104207
patent document 2: WO 2015/199243

Non-Patent Documents non-patent document 1: Jin, Y. et al., Microbiology, 155: 35-45 (2009)
non-patent document 2: Matsumura, T. et al., Cell Microbiol., 10: 355-364 (2008)
non-patent document 3: Sugawara, Y. et al., J. Cell. Biol., 189: 691-700 (2010)
non-patent document 4: Amatsu, S. et al., J. Biol. Chem., 288: 35617-35625 (2013)
non-patent document 5: Lee, K. et al., PLoS Pathog., 9: e1003690 (2013)
non-patent document 6: Lee, K. et al., Science, 344: 1405-1410 (2014)

SUMMARY OF INVENTION

Technical Problem

Therefore, the purpose of the present invention is to provide a novel miniaturized HA complex protein maintaining cadherin function inhibitory activity, and provide a convenient means of maintaining an undifferentiated state of pluripotent stem cells at a low cost using the protein.

Solution to Problem

In an attempt to achieve the above-mentioned goal, the present inventors have tried two types of HA miniaturization strategy.

Firstly, mini-HA complex (containing Glu at position 380 to Asn at position 626 as HA3 fragment) which is similar to the one produced by Jin et al. was investigated for the cadherin function inhibitory activity using the transepithelial electrical resistance (TER) in cultured cells as an index. Surprisingly, it was found that the mini-HA complex lowers TER like FL-HA and has cadherin function inhibitory activity (see FIG. 1, FIG. 2).

Secondly, since it was clear from the results of pull-down assay and crystal structure analysis that the HA region that contributes to the binding with E-cadherin is the HA2-HA3 connecting region (see, for example, non-patent documents 3 and 4), full-length HA2 and HA3 were respectively expressed, mixed, reconstituted into HA2:HA3=3:3 HA complex (FL(2+3)), and examined for TER in cultured cells. As a result, TER decreased and it was found that a trivalent complex maintains cadherin function inhibitory activity even in the absence of HA1 subcomponent (see FIG. 1, FIG. 3). Furthermore, it was clarified that even when HA2 and HA3 are expressed as a fusion protein via a linker (linked-FL(2+3)), the cadherin function inhibitory activity is maintained, and functional HA2:HA3=3:3 HA complex can be easily produced without mixing and incubating after once purifying each subcomponent.

Furthermore, the present inventors similarly deleted HA1 subcomponent and further tried to achieve miniaturization also in the above-mentioned first HA miniaturization strategy. However, the cadherin function inhibitory activity disappeared in a HA complex obtained by deleting HA1 subcomponent from mini-HA complex (mini(2+3)) (see FIG. 1, FIG. 3).

The HA subcomponents used heretofore were all derived from *Clostridium botulinum* type B. The present inventors replaced the HA2 subcomponent in the mini(2+3) complex with that derived from HA of *Clostridium botulinum* type C, which is known not to interact with E-cadherin or disrupt the intercellular barrier of the human intestinal epithelial cell line (mini(2+3)/CB). As a result, surprisingly, a decrease in TER was observed though temporarily and transient cadherin function inhibitory activity was shown (see FIG. 1, FIG. 4).

Then, similar to the case of the FL(2+3) complex, the present inventors expressed each of mini(2+3) and mini(2+3)/CB with HA2 and HA3 as fusion proteins (linked-mini (2+3)/BB, linked-mini(2+3)/CB, respectively). Cadherin function inhibitory activity was exhibited even when HA2 subcomponent of type B was used by linking with a linker (see FIG. 1, FIG. 5). When HA2 subcomponent of type C was used, the transient cadherin function inhibitory activity changed to sustained activity by linking with a linker (see FIG. 1, FIG. 6, FIG. 7).

Furthermore, the present inventors introduced a mutation that substitutes each of 1 to several hydrophobic amino acid residues exposed on the surface of the molecules of the above-mentioned linked-mini(2+3)/CB with more hydrophilic amino acids (linked-mini(2+3)/CB-YFDY, linked-mini(2+3)/CB-LD/YFDY). As a result, by introducing these mutations, the cadherin function inhibitory activity was further improved, and the activity similar to that of the mini-HA complex was exhibited (see FIG. 1, FIG. 7). In addition, it was also confirmed that these mutation-introduced miniaturized HA complexes showed about 10 times or more improved yield as compared to an FL-HA expression system obtained by respectively producing three full-length HA subcomponents, mixing and reconstituting the subcomponents.

The present inventors then investigated whether linked-mini (2+3)/CB-LD/YFDY can, like FL-HA, inhibit the cell-cell adhesion of iPS cells, and confirmed that it inhibits the cell-cell adhesion at a concentration of at least 50 nM (see FIGS. 16A and 16B). In addition, the linked-mini (2+3)/CB-LD/YFDY showed a cell proliferation promoting action equivalent to FL-HA at the same molar concentration, and about 3 times stronger cell proliferation promoting action than FL-HA in terms of weight/volume concentration per single arm (protomer).

The present inventors conducted further studies based on these findings, and completed the present invention.

Accordingly, the present invention provides the following.

[1] A miniaturized hemagglutinin complex protein having function inhibitory activity against E-cadherin, wherein
(a) all or a part of at least HA1 subcomponent, and/or a part of HA3 subcomponent are/is deleted,
(b) regions in HA2 and HA3 subcomponents that contribute to binding with E-cadherin are present, and
(c) the HA3 subcomponent is derived from *Clostridium botulinum* type A or type B,
provided that a monovalent complex protein consisting of a full-length HA1 subcomponent dimer, a full-length HA2 subcomponent and a fragment of Pro at position 378 to Asn at position 626 of HA3 subcomponent, each derived from *Clostridium botulinum* type A, in association is excluded.

[2] The hemagglutinin complex protein of the above-mentioned [1] that is monovalent.

[3] The hemagglutinin complex protein of the above-mentioned [2], wherein the HA3 subcomponent part is
(a) the amino acid sequence shown in SEQ ID NO: 1 or 2, or
(b) the amino acid sequence wherein 1 to several amino acids are substituted, deleted, inserted or added.

[4] The hemagglutinin complex protein of the above-mentioned [2] or [3], wherein the HA2 subcomponent part is
(a) the amino acid sequence shown in any of SEQ ID NO: 3-6, or
(b) the amino acid sequence wherein 1 to several amino acids are substituted, deleted, inserted or added.

[5] The hemagglutinin complex protein of any of the above-mentioned [2] to [4], wherein the HA1 subcomponent is entirely deleted.

[6] The hemagglutinin complex protein of any of the above-mentioned [2] to [5], wherein the HA3 subcomponent and the HA2 subcomponent are linked via a linker.

[7] The hemagglutinin complex protein of the above-mentioned [6], wherein the C-terminal of HA3 subcomponent and the N-terminal of HA2 subcomponent are linked via a linker.

[8] The hemagglutinin complex protein of any of the above-mentioned [2] to [7], wherein the HA2 subcomponent is derived from *Clostridium botulinum* type C or type D.

[9] The hemagglutinin complex protein of any of the above-mentioned [2] to [8], wherein each of 1 to several hydrophobic amino acid residues which are exposed on the surface of the molecules of the hemagglutinin complex protein and are amino acid residues in the HA2 subcomponent and/or HA3 subcomponent is substituted by a more hydrophilic amino acid.

[10] The hemagglutinin complex protein of the above-mentioned [1] that is trivalent.

[11] The hemagglutinin complex protein of the above-mentioned [10], wherein the HA1 subcomponent is entirely deleted.

[12] The hemagglutinin complex protein of the above-mentioned [10] or [11], wherein the HA2 subcomponent is
(a) the amino acid sequence shown in any of SEQ ID NO: 3-6, or
(b) the amino acid sequence wherein 1 to several amino acids are substituted, deleted, inserted or added.

[13] The hemagglutinin complex protein of any of the above-mentioned [10] to [12], wherein the HA3 subcomponent is
(a) a sequence comprising at least a partial sequence of amino acid numbers 19 to 626 in the amino acid sequence shown in SEQ ID NO: 7 or 8, or
(b) the amino acid sequence wherein 1 to several amino acids are substituted, deleted, inserted or added.

[14] The hemagglutinin complex protein of any of the above-mentioned [10] to [13], wherein the HA3 subcomponent and the HA2 subcomponent are linked via a linker.

[15] The hemagglutinin complex protein of the above-mentioned [14], wherein the C-terminal of HA3 subcomponent and the N-terminal of HA2 subcomponent are linked via a linker.

[16] A nucleic acid encoding the hemagglutinin complex protein of any of the above-mentioned [1] to [15].

[17] An expression vector comprising the nucleic acid of the above-mentioned [16].

[18] A host cell comprising the expression vector of the above-mentioned [17] introduced thereinto.

[19] A method for producing a hemagglutinin complex protein comprising culturing the host cell of the above-mentioned [18], collecting a hemagglutinin complex protein or a subcomponent thereof from the obtained culture, in the case of the subcomponent, further contacting the obtained subcomponents with each other and collecting the hemagglutinin complex protein produced thereby.

[20] An E-cadherin function inhibitor comprising the hemagglutinin complex protein of any of the above-mentioned [1] to [15], or a monovalent complex protein consisting of a *Clostridium botulinum* type A-derived full-length HA1 subcomponent dimer, a full-length HA2 subcomponent and a fragment of Pro at position 378 to Asn at position 626 of HA3 subcomponent in association.

[21] The inhibitor of the above-mentioned [20], wherein the function of E-cadherin is a cell-cell adhesion function.

[22] A method for inhibiting cell-cell adhesion in a cell population comprising bringing the hemagglutinin complex protein of any of the above-mentioned (1) to [15], or a monovalent complex protein consisting of a full-length HA1 subcomponent dimer, a full-length HA2 subcomponent and a fragment of Pro at position 378 to Asn at position 626 of HA3 subcomponent, each derived from *Clostridium botulinum* type A, in association into contact with the cell population.

[23] The method of the above-mentioned [22], wherein the cell population is a population of pluripotent stem cells.

[24] A cell proliferation promoter comprising the hemagglutinin complex protein of any of the above-mentioned [1] to [15], or a monovalent complex protein consisting of a full-length HA1 subcomponent dimer, a full-length HA2 subcomponent and a fragment of Pro at position 378 to Asn at position 626 of HA3 subcomponent, each derived from *Clostridium botulinum* type A, in association.

[25] A method for promoting proliferation of a cell comprising culturing the cell in the presence of the hemagglutinin complex protein of any of the above-mentioned [1] to [15], or a monovalent complex protein consisting of a full-length HA1 subcomponent dimer, a full-length HA2 subcomponent and a fragment of Pro at position 378 to Asn at position 626 of HA3 subcomponent, each derived from *Clostridium botulinum* type A, in association.

Advantageous Effects of Invention

According to the present invention, a miniaturized novel HA complex protein maintaining cadherin function inhibitory activity is provided. Therefore, an HA complex protein for maintaining an undifferentiated state of pluripotent stem cells including iPS cells can be provided conveniently at a low cost, and is extremely useful.

BRIEF DESCRIPTION OF DRAWINGS

FIG. 8 is a drawing showing the effects of a linked-mini (2+3)/CB-YFDY complex and a linked-mini (2+3)/CB-YFDY/ITCC complex on the TER value in cultured Caco-2 cells.

FIG. 9 is a drawing showing the effects of a mini-HA complex on the cell-cell adhesion of cultured MDCK cells.

FIG. 15 is a drawing showing the amino acid sequence of a linked-mini (2+3)/CB-LD/YFDY complex (SEQ ID NO: 50).

FIG. 16A shows the experiment protocol. FIG. 16B is a microscopic photograph showing the cell-cell adhesion inhibitory effect of various concentrations (0.5 to 100 nM) of the FL-HA complex of type B and linked-mini (2+3)/CB-LD/YFDY complex on day 3 from the start of culture (Day3).

DESCRIPTION OF EMBODIMENTS

Figure 1:
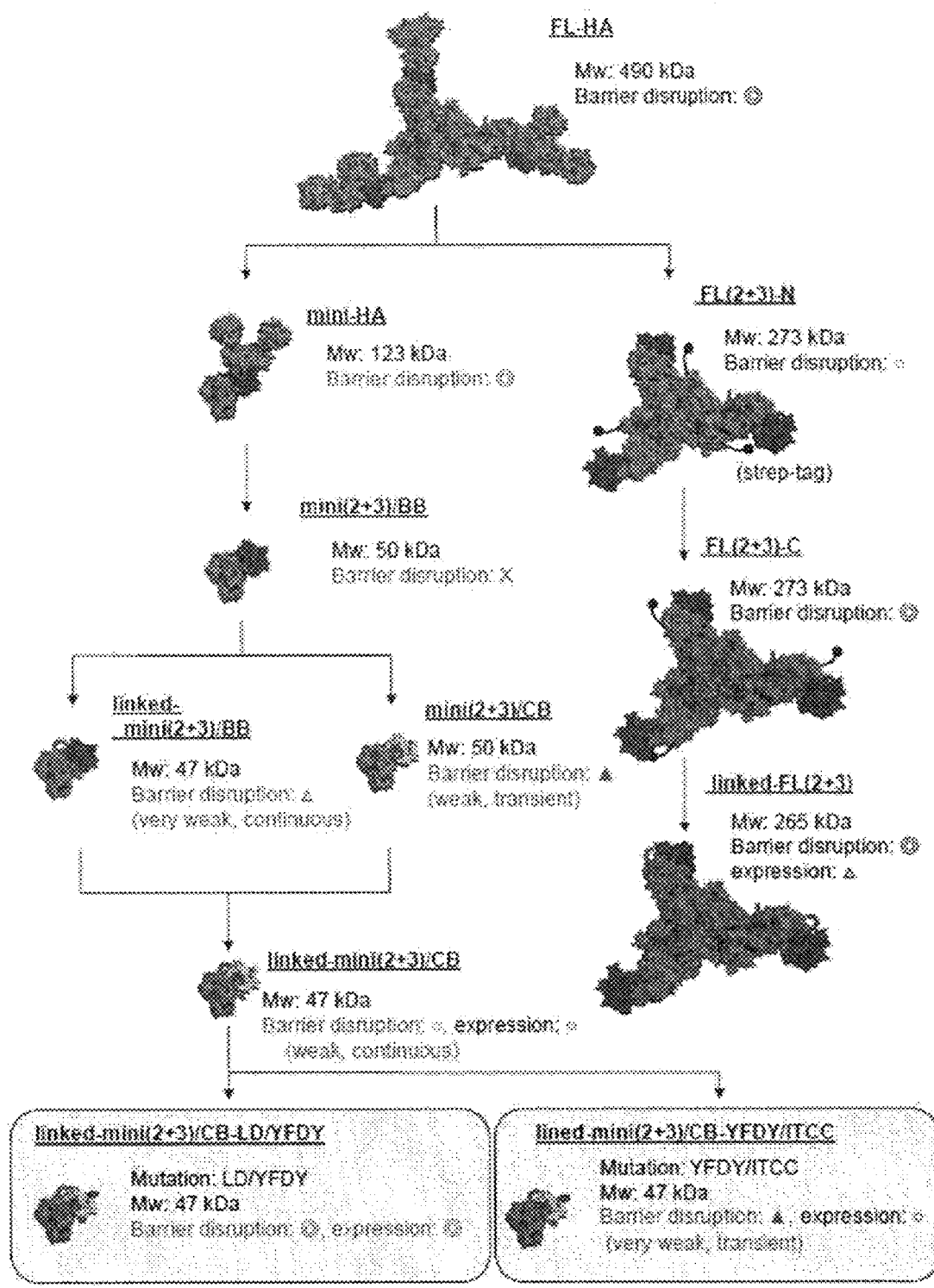
FIG. 1 is a flow diagram schematically showing the miniaturization strategy of the HA complex protein of the present invention.

The present invention provides a miniaturized HA complex protein having function inhibitory activity against E-cadherin (hereinafter to be also referred to as "the HA complex of the present invention"). The HA complex protein is characterized in that
(a) all or a part of at least HA1 subcomponent, and/or a part of HA3 subcomponent are/is deleted,
(b) regions in HA2 and HA3 subcomponents that contribute to binding with E-cadherin is present, and
(c) the HA3 subcomponent is derived from *Clostridium botulinum* type A or type B.

The HA complex of the present invention is largely divided into a monovalent type and a trivalent type.

(I) Monovalent HA Complex

In the present specification, the "monovalent" includes a complex consisting of an HA1 subcomponent dimer, an HA2 subcomponent and an HA3 subcomponent as a base (whole type), wherein a part or all of one or more subcomponents is/are deleted. A trivalent HA complex is formed by trimerizing a monovalent HA complex having a triskelion-like conformation, and a whole monovalent HA complex that underwent trimerization is FL-HA (12-mer). It is theoretically impossible to form a triskelion-like trivalent HA complex due to deletion of the N-terminal region of the HA3 subcomponent. Even when two or more monovalent HA complexes are present in association with each other due to some intermolecular interaction, they are included in the monovalent HA complex of the present invention.

The monovalent HA complex of the present invention contains at least regions in HA2 and HA3 subcomponents that contribute to the binding with E-cadherin.

The region in the HA2 subcomponent that contributes to the binding with E-cadherin may be a region containing amino acid residues at positions 83, 86, 104, 109, 131 and 135 which form a hydrogen bond or salt bridge with E-cadherin (see, for example, non-patent document 6). For example, it may be a region containing an amino acid sequence of 80- to 135-positions, preferably 50- to 140-positions, more preferably 2- to 146-positions, of the HA2 subcomponent.

The region in the HA3 subcomponent that contributes to the binding with E-cadherin may be a region containing amino acid residues at positions 501, 503, 505, 506, 534, 535, 582, 586, 607 and 609 which form a hydrogen bond or salt bridge with E-cadherin, and further, a region containing amino acid residues at positions 417, 473 and 508 which are involved in hydrophobic interactions with E-cadherin (see, for example, non-patent document 6), for example, a region containing an amino acid sequence of 400- to 610-positions, preferably 390- to 620-positions, more preferably 380- to 626-positions, of the HA3 subcomponent.

The HA3 subcomponent constituting the monovalent HA complex of the present invention may include an amino acid sequence further on the N-terminal side from the 380-position. When an amino acid sequence further on the C-terminal side than the 380-position is present, function inhibitory activity against E-cadherin can be imparted to the complex. Thus, in one preferable embodiment, from the aspect of miniaturization, the HA3 subcomponent does not contain an amino acid sequence on the N-terminal side from the 380-position. In an embodiment in which each subcomponent is produced separately and then contacted with each other to allow for reconstitution, inclusion of up to the further N-terminal side of the HA3 subcomponent may cause reconstitution into a trivalent form and lower the yield of the monovalent form. Also from this respect, it is desirable not to include an amino acid sequence further on the N-terminal side than the 380-position.

The HA3 subcomponent constituting the monovalent HA complex of the present invention is derived from *Clostridium botulinum* type A or type B. Examples of the HA3 subcomponent derived from *Clostridium botulinum* type A include a protein having the amino acid sequence shown in SEQ ID NO: 7 (GenBank: AAM75949.1). Examples of the HA3 subcomponent derived from *Clostridium botulinum* type B include a protein having the amino acid sequence shown in SEQ ID NO: 8 (GenBank: ACA46977.1). The HA3 subcomponent derived from *Clostridium botulinum* type A or type B also includes the amino acid sequence shown in SEQ ID NO: 7 or 8 wherein 1 to several (e.g., 2, 3, 4, 5, 6, 7, 8, 9 or 10) amino acids are substituted, deleted, inserted or added. Since the HA3 subcomponent of type A and the HA3 subcomponent of type B have about 98% amino acid identity, examples of the positions at which amino acids are substituted, deleted, inserted or added include positions at which amino acid residues are different between the HA3 of type A and the HA3 of type B. Alternatively, the position of the mutation may be a hydrophobic amino acid residue exposed on the molecular surface of the below-mentioned HA complex protein. When an amino acid residue in the HA3 subcomponent is replaced with another amino acid, it is desirably replaced with a similar amino acid. The "similar amino acid" means an amino acid similar in physicochemical properties and, for example, amino acids classified in the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having hydroxyl group (Ser, Thr), amino acids with small side chain (Gly, Ala, Ser, Thr, Met) and the like can be mentioned. Substitution with such similar amino acids is expected to prevent changes in the phenotype of the protein (i.e., conservative amino acid substitution). Specific examples of conservative amino acid substitution are well known in the art and described in various literatures (e.g., Bowie et al., Science, 247:1306-1310 (1990)).

Therefore, the HA3 subcomponent constituting the monovalent HA complex of the present invention may include, for example, a partial amino acid sequence of the 400- to 610-position, preferably 390- to 620-position, more preferably 380- to 626-position, of the amino acid sequence shown in SEQ ID NO: 7 or 8, or the partial amino acid sequence wherein 1 to several amino acids are substituted, deleted, inserted or added.

In one embodiment, the monovalent HA complex of the present invention may contain the HA2 subcomponent and the HA3 subcomponent, and further, a HA1 subcomponent. The HA1 subcomponent may be derived from any of *Clostridium botulinum* type A to type D, desirably derived from *Clostridium botulinum* type A or type B, more desirably derived from *Clostridium botulinum* type B. Examples of the HA1 subcomponent derived from *Clostridium botulinum* type A include a protein having the amino acid sequence shown in SEQ ID NO: 9 (GenBank: AAM75951.1). Examples of the HA1 subcomponent derived from *Clostridium botulinum* type B include a protein having the amino acid sequence shown in SEQ ID NO: 10 (GenBank: ACA46991.1). Examples of the HA1 subcomponent derived from *Clostridium botulinum* type C include a protein having the amino acid sequence shown in SEQ ID NO: 11 (NCBI reference Sequence: YP_398514.1). Examples of the HA1 subcomponent derived from *Clostridium botulinum* type D include a protein having the amino acid sequence shown in SEQ ID NO: 12 (GenBank: EES90382.1). The HA1 subcomponent derived from any of

*Clostridium botulinum* type A to type D also includes the amino acid sequence shown in any of SEQ ID NO: 9-12 wherein 1 to several (e.g., 2, 3, 4, 5, 6, 7, 8, 9 or 10) amino acids are substituted, deleted, inserted or added. While the substitution, deletion, insertion and addition of the amino acids are basically the same as those in the aforementioned HA3 subcomponent, since the HA1 subcomponent may be derived from *Clostridium botulinum* type C or type D, the positional freedom of mutations may be higher than that of the HA3 subcomponent. That is, the HA1 subcomponent of type A and the HA1 subcomponent of type B have about 84% amino acid identity, the HA1 subcomponent of type B and the HA1 subcomponent of type C or type D respectively have about 35%, about 40% amino acid identities, and 56%, 58% amino acid identities at most even when similar amino acids are included. Thus, for example, there are more positions where amino acid residues are different between HA2 of type A or type B and HA2 of type C or type D, as the positions where amino acids are substituted, deleted, inserted or added. When an amino acid residue in the HA1 subcomponent is substituted by another amino acid, it is desirable to substitute with a similar amino acid. Examples of the "similar amino acid" include those similar to the above. When an amino acid residue in the HA1 subcomponent is deleted, for example, 1 to several (e.g., 2, 3, 4, 5, 6, 7, 8, 9 or 10) amino acids on the N-terminal may be deleted.

The HA1 subcomponent may contain the full length thereof, or a part thereof alone. When a part thereof alone is contained, it is desirable to contain at least a region that contributes to the interactions with E-cadherin. The monovalent HA complex may contain the HA1 subcomponent as a so dimer or a monomer.

In one preferable embodiment, the monovalent HA complex of the present invention contains full-length HA1 subcomponent in a dimer. A monovalent complex protein containing a full-length HA1 subcomponent dimer, a full-length HA2 subcomponent, and a fragment of Pro at position 378 to Asn at position 626 of HA3 subcomponent, each derived from *Clostridium botulinum* type A, in association (mini-HA complex of Jin et al.) has been conventionally reported to bind with E-cadherin but have no barrier disruption activity. However, the present inventors have found that the mini-HA complex has cadherin function inhibitory activity same as that of whole HA 12-mer (FL-HA).

In a preferable embodiment, the monovalent HA complex of the present invention is a complex protein wherein the HA3 subcomponent part is
(a) the amino acid sequence shown in SEQ ID NO: 1 or 2, or
(b) the amino acid sequence wherein 1 to several amino acids are substituted, deleted, inserted or added.

The amino acid sequences of SEQ ID NO: 1 and 2 respectively correspond to the amino acid sequence at positions 380 to 626 of the amino acid sequences of SEQ ID NO: 7 and 8. The substitution, deletion, insertion and addition of the amino acids are basically the same as those in the above.

In another preferable embodiment, the monovalent HA complex of the present invention is a complex protein wherein the HA2 subcomponent part is
(a) the amino acid sequence shown in any of SEQ ID NO: 3-6, or
(b) the amino acid sequence wherein 1 to several amino acids are substituted, deleted, inserted or added.

The amino acid sequences of SEQ ID NO: 3-6 respectively correspond to the full-length (positions 1 to 146) amino acid sequence (GenBank: AAM75950.1, GenBank: BAE48260.1, NCBI: YP_398513.1 and GenBank: EES90370.1, respectively) of the HA2 subcomponent derived from *Clostridium botulinum* type A-type D. The substitution, deletion, insertion and addition of the amino acids are basically the same as those in the aforementioned HA3 subcomponent. Since the HA2 subcomponent may be derived from *Clostridium botulinum* type C or type D, the positional freedom of mutations may be higher than that of the HA3 subcomponent. That is, the HA2 subcomponent of type A and the HA2 subcomponent of type B have about 98% amino acid identity, the HA2 subcomponent of type B and the HA2 subcomponent of type C or type D have 64% amino acid identity, and 79% amino acid identity at most even when similar amino acids are included (see FIG. 12). Thus, for example, there are more positions where amino acid residues are different between HA2 of type A or type B and HA2 of type C or type D, as the positions where amino acids are substituted, deleted, inserted or added.

In the monovalent HA complex of the present invention, the respective HA subcomponents may be expressed as separate proteins and contacted with each other to allow for reconstitution, or may be expressed as a fusion protein via a linker. In the latter case, the production step can be simplified since purification, reconstitution or further purification of each subcomponent is not necessary.

In another preferable embodiment, HA1 subcomponent is entirely deleted from the monovalent HA complex of the present invention. By deleting whole HA1 subcomponent, the molecular weight of the monovalent HA complex can be reduced to not more than half (about 50 kDa). In the embodiment including expression of the HA2 subcomponent and the HA3 subcomponent as separate proteins, followed by reconstitution, an HA2 subcomponent derived from *Clostridium botulinum* type C or type D needs to be used. This is because function inhibitory activity against E-cadherin may disappear from the monovalent HA complex obtained using an HA2 subcomponent of type A or type B.

Therefore, in one preferable embodiment, the monovalent HA complex of the present invention contains an HA2 subcomponent derived from *Clostridium botulinum* type C.

In another preferable embodiment, the monovalent HA complex of the present invention may be provided as a fusion protein in which an HA3 subcomponent and an HA2 subcomponent are linked via a linker. When provided as a fusion protein, function inhibitory activity against E-cadherin can be imparted to an HA complex even by using an HA2 subcomponent derived from *Clostridium botulinum* type A or type B. When an HA2 subcomponent derived from *Clostridium botulinum* type C or type D is used, the transient cadherin function inhibitory activity can be changed to that in a sustained manner. By expressing as a fusion protein, mixing of contaminants and/or decomposed products can be suppressed, HA complex can be purified at high purity (see FIG. 11), and the yield is remarkably improved, as in the case of separate expression of respective subcomponents, followed by reconstitution.

Figure 13:
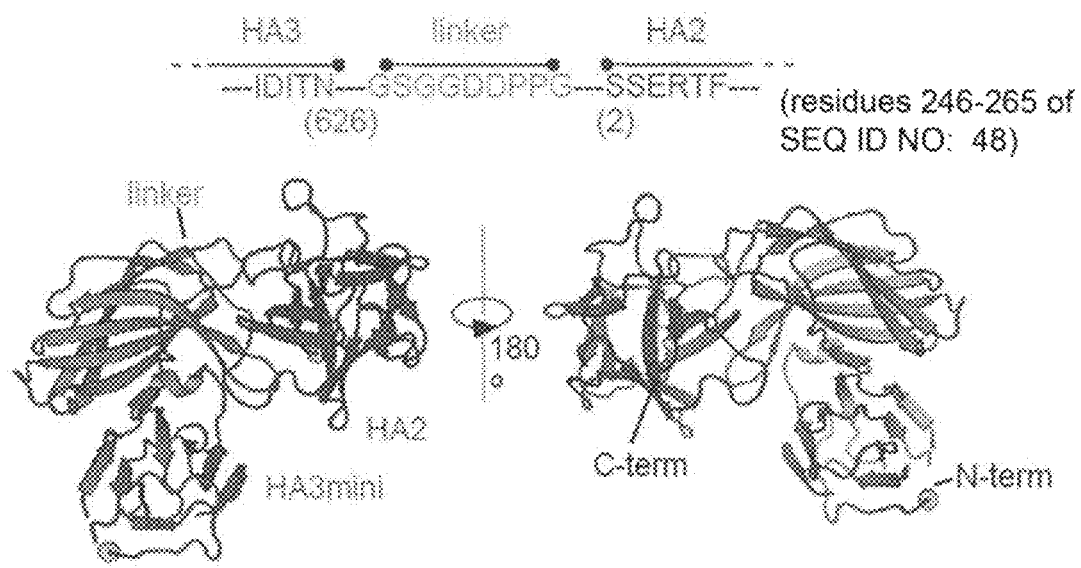
FIG. 13 is a schematic drawing showing the conformation of a linked-mini (2+3) complex. The linker sequence is the sequence of SEQ ID NO: 13.

The linker is not particularly limited as long as it is a peptide linker. In consideration of the conformation of the HA2 subcomponent and the HA3 subcomponent (see FIG. 13), when the C-terminal of the HA3 subcomponent and the N-terminal of the HA2 subcomponent are linked via a linker, a linker composed of any amino acid sequence consisting of 6-12 amino acids, preferably 8-10 amino acids, can be used. Examples thereof include, but are not limited to, GSGGDDPPG (SEQ ID NO: 13).

On the other hand, when the C-terminal of the HA2 subcomponent and the N-terminal of the HA3 subcomponent are linked via a linker, since the both terminals are distant in the conformation of the HA complex, a longer linker is desirably used. It is more preferable to connect the C-terminal of the HA3 subcomponent and the N-terminal of the HA2 subcomponent with a linker, in view of disadvantages such as easy cleavage of the linker by protease or peptidase.

Figure 14:
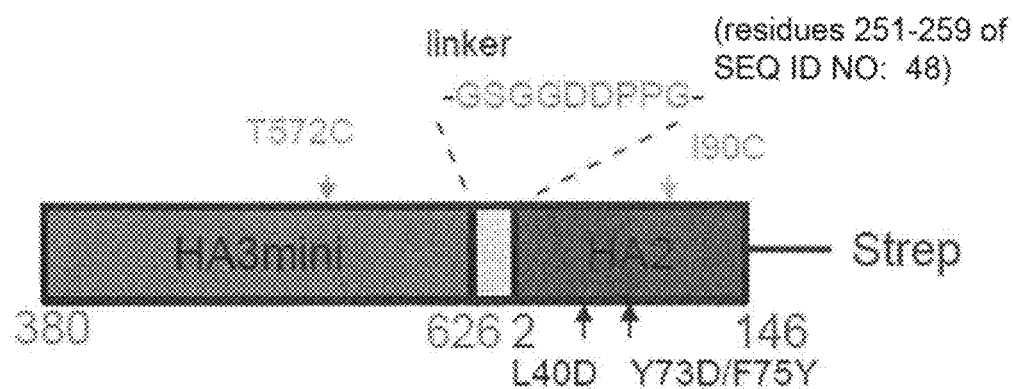
FIG. 14 is a schematic drawing showing introduction of various mutations into a linked-mini (2+3)/CB complex. The linker sequence is the sequence of SEQ ID NO: 13.

In yet another preferable embodiment of the present invention, the monovalent HA complex of the present invention can further improve barrier disruption activity by substituting 1 to several hydrophobic amino acid residues exposed on the molecular surface thereof with more hydrophilic amino acids. Examples of the hydrophobicity amino acid when the HA complex is mini-HA(2+3)/CB include F7, F19, L23, L35, L40, I50, V61, A62, Y70, Y73, F75, Y77, L86, I90, I94, L102, I104, V105, V107, Y110, Y115, I121, L127, L129, F132, I134, and L146 in the HA2 subcomponent, and I383, Y393, I397, F406, Y407, L409, I417, L426, I435, G436, I437, Y457, I458, A466, L473, Y481, I491, M508, I514, Y525, V533, Y558, Y561, I565, F569, I575, I581, I583, L590, I596, L599, I603, L613, Y616 and the like in the HA3 subcomponent. Preferable examples thereof include, but are not limited to, substitution of the Leu residue at the 40-position of HA2 with Asp, the Tyr residue at the 73-position 25 with Asp, the Phe residue at the 75-position with Tyr and the like (FIGS. 14 and 15).

In another embodiment of the present invention, a cysteine residue can be introduced into each subcomponent. For example, the Thr residue at the 572-position of the HA3 subcomponent and/or the Ile residue at the 90-position of the HA2 subcomponent can be respectively substituted with Cys (linked-mini(2+3)-YFDY/ITCC, FIGS. 14 and 15). By the mutation, it is possible to change the sustained barrier disruption activity achieved by linking the HA2 subcomponent and the HA3 subcomponent with a linker to transient activity.

(II) Trivalent HA Complex

The present invention also provides the trivalent HA complex protein. The trivalent HA complex does not prevent deletion of a part of the HA3 subcomponent, but it needs to contain a region that contributes to binding with E-cadherin and a region necessary for taking a triskelion-like conformation. The region that contributes to binding with E-cadherin is the same as that in the case of the aforementioned monovalent form. To be reconstituted as a trivalent form, the region needs to include the amino acid sequence on the N-terminal side of the HA3 subcomponent. Therefore, in a preferable embodiment, the trivalent HA complex may contain the full length HA3 subcomponent.

The HA2 subcomponent constituting the trivalent HA complex of the present invention may be a fragment as long as it contains a region that contributes to binding with E-cadherin in the subcomponent. The region that contributes to binding with E-cadherin region is the same as that in the aforementioned monovalent HA complex.

In a preferable embodiment, HA1 subcomponent is entirely deleted from the trivalent HA complex of the present invention. By deleting whole HA1 subcomponent, the molecular weight of the trivalent HA complex can be reduced to close to a half (about 270 kDa).

Regardless of whether the HA complex of the present invention is a monovalent form or a trivalent form, it may have a tag on the terminal to facilitate purification or when it is used for, example, maintaining undifferentiated pluripotent stem cells, to ensure rapid removal after achieving the purpose. Examples of the tag include, but are not limited to, FLAG tag, His tag, Strep tag and the like. The tag may be attached to the N-terminal of each HA subcomponent or may be added to the C-terminal. In the trivalent HA complex of the present invention, addition of a tag to the N-terminal side of HA3 may lower the cadherin function inhibitory activity, and therefore, a tag is preferably added to the C-terminal side of HA3.

In a preferable embodiment, the trivalent HA complex of the present invention is a complex protein wherein the HA2 subcomponent is
(a) the amino acid sequence shown in any of SEQ ID NO: 3-6, or
(b) the amino acid sequence wherein 1 to several amino acids are substituted, deleted, inserted or added.

As mentioned above, the amino acid sequences of SEQ ID NO: 3-6 respectively correspond to the full-length (positions 1 to 146) amino acid sequence of the HA2 subcomponent of type A to type D. The substitution, deletion, insertion and addition of the amino acids are basically the same as those in the above.

In another preferable embodiment, the trivalent HA complex of the present invention is a complex protein wherein the HA3 subcomponent part is
(a) the amino acid sequence shown in SEQ ID NO: 7 or 8 comprising at least a partial sequence of amino acid numbers 19 to 626 (used in Examples), or
(b) the amino acid sequence wherein 1 to several amino acids are substituted, deleted, inserted or added.

The amino acid sequences of SEQ ID NO: 7 and 8 respectively correspond to the full-length amino acid sequences of the HA3 subcomponent of type A and type B. The substitution, deletion, insertion and addition of the amino acids are the same as those in the HA3 subcomponent in the aforementioned monovalent HA complex.

In the trivalent HA complex of the present invention, an HA3 subcomponent and an HA2 subcomponent may also be linked via a linker, as in the aforementioned monovalent HA complex. Examples of the linker include those similar to the above. In addition, the C-terminal of the HA3 subcomponent and the N-terminal of the HA2 subcomponent are preferably linked via a linker, as in the monovalent HA complex.

(III) Production of the HA Complex Protein of the Present Invention

The HA complex protein of the present invention can be produced by introducing an expression vector containing a DNA encoding each subcomponent or a fusion protein thereof into a host cell, culturing same, collecting the subcomponent or fusion protein from the obtained culture, in the case of the subcomponent, further contacting the obtained subcomponents with each other and collecting the HA complex protein produced thereby.

The DNA encoding each subcomponent can be cloned by, for example, synthesizing based on the cDNA sequence information thereof an oligo DNA primer covering the region encoding the desired portion of the protein, and amplifying by a (RT-)PCR method using, as a template, genomic DNA or mRNA fraction prepared from *Clostridium botulinum* that produces the protein.

The cloned DNA may be ligated as it is or may be digested with a restriction enzyme on demand or added with an appropriate linker and ligated with a DNA encoding other subcomponents, whereby a DNA encoding a fusion protein can be prepared.

An expression vector containing a DNA encoding each subcomponent or a fusion protein thereof can be produced, for example, by ligating the DNA at the downstream of a promoter in a suitable expression vector.

As the expression vector, plasmid derived from *Escherichia coli* (e.g., pBR322, pBR325, pUC12, pUC13); plasmid derived from *Bacillus subtilis* (e.g., pUB110, pTP5, pC194); plasmid derived from yeast (e.g., pSH19, pSH15); insect cell expressing plasmid (e.g., pFast-Bac); animal cell expressing plasmid (e.g., pA1-11, pXT1, pRc/CMV, pRc/RSV, pcDNAI/Neo); bacteriophage such as λphage and the like; insect virus vector such as baculovirus and the like (e.g., BmNPV, AcNPV); animal virus vector such as retrovirus, vaccinia virus, adenovirus and the like, and the like are used.

The promoter may be any as long as it is an appropriate promoter for the host used for gene expression. For example, when the host is an animal cell, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (herpes simplex virus thymidine kinase) promoter and the like are used. Among these, CMV promoter, SRα promoter and the like are preferable. When the host is *Escherichia coli*, trp promoter, lac promoter, recA promoter, $AP_L$ promoter, lpp promoter, T7 promoter and the like are preferable. When the host is genus *Bacillus*, SPO1 promoter, SPO2 promoter, penP promoter and the like are preferable. When the host is yeast, Gal1/10 promoter, PH05 promoter, PGK promoter, GAP promoter, ADH promoter and the like are preferable.

As the expression vector, one containing, when desired, enhancer, splicing signal, terminator, poly A addition signal, selection marker of drug resistance gene, complementing auxotrophic complementing gene and the like can be used besides those mentioned above.

RNA encoding each subcomponent or a fusion protein thereof of the HA complex protein of the present invention can be prepared, for example, by transcription into mRNA in an in vitro transcription system known per se and using a vector encoding the DNA encoding the above-mentioned each subcomponent or a fusion protein thereof as a template.

An expression vector containing a DNA encoding each subcomponent or a fusion protein thereof is introduced into a host cell, and the host cell is cultured, whereby the subcomponent or fusion protein can be expressed in the host cell.

As the host, for example, *Escherichia coli*, genus *Bacillus*, yeast, insect cell, insect, animal cell, and the like are used. As the *Escherichia coli, Escherichia coli* K12 DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used. As the genus *Bacillus, Bacillus subtilis* MI114 [Gene, 24, 255 (1983)], *Bacillus subtilis* 237-21 [Journal of Biochemistry, 95, 87 (1984)] and the like are used. As the yeast, *Saccharomyces cerevisiae* AH22, AH22R, NA87-11A, DKD-5D, 20B-12, *Schizosaccharomyces pombe* NCYC1913, NCYC2036, *Pichia pastoris=Komagataella phaffii* KM71 and the like are used.

Introduction of an expression vector can be performed by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host. *Escherichia coli* can be transformed according to the methods described in, for example, Proc. Natl. Acad. Sci. USA, 69, 2110 (1972), Gene, 17, 107 (1982) and the like. The genus *Bacillus* can be introduced into a vector according to the method described in, for example, Molecular& General Genetics, 168, 111 (1979) and the like. The yeast can be introduced into a vector according to the method described in, for example, Methods in Enzymology, 194, 182-187 (1991), Proc. Natl. Acad. Sci. USA, 75, 1929 (1978) and the like.

The cells having a vector introduced therein can be cultured by a known method according to the kind of the host. For example, when *Escherichia coli* or genus *Bacillus* is cultured, the medium is preferably a liquid medium. The medium preferably contains carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. In addition, the medium may contain yeast extract, vitamins, growth promoting factor and the like. The pH of the medium is preferably about 5-about 8.

When *Escherichia coli* is cultured, the medium is preferably M9 medium containing glucose and casamino acid [Journal of Experiments in Molecular Genetics, 431-433, Cold Spring Harbor Laboratory, New York 1972]. Where necessary, an agent such as 30-indolylacrylic acid may be added to the medium to ensure efficient action of the promoter. *Escherichia coli* is cultured generally at about 15-about 43° C. Where necessary, aeration and stirring may be performed.

The genus *Bacillus* is cultured generally at about 30-about 40° C. Where necessary, aeration and stirring may be performed.

When the yeast is cultured, the medium is preferably a Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] or the like. The pH of the medium is preferably about 5-about 8. The culture is performed generally at about 20° C.-about 35° C. Where necessary, aeration and stirring may be performed.

As described above, each subcomponent or a fusion protein thereof can be expressed in a host cell. These proteins can be recovered and purified easily by using an antibody against them, or when a tag is added to the protein, using a substance specific to the tag, for example, by immobilizing them on a carrier, and bringing the obtained culture of the host cell into contact with the carrier. In addition, these proteins may be purified by appropriately combining separation and purification methods of any other proteins known per se.

When respective subcomponents are expressed as separate proteins, the respective subcomponents are purified by the above-mentioned method, mixed according to a conventional method, and incubated under appropriate conditions, whereby they can be reconstituted into the HA complex protein of the present invention.

(IV) Use of the HA Complex Protein of the Present Invention

In the HA complex protein of the present invention, the function of E-cadherin, preferably intercellular barrier function inhibitory activity (i.e., barrier disruption activity) is maintained and the molecular size is miniaturized. Thus, the HA complex protein is easily produced, is superior in handling, and can be used more advantageously in the use of conventionally-known HA complex protein than the conventional products.

Therefore, the present invention also provides an E-cadherin function inhibitor containing the HA complex protein of the present invention (hereinafter to be also referred to as "the inhibitor of the present invention"). Particularly, the inhibitor of the present invention is useful in inhibiting the cell-cell adhesion function of E-cadherin and may be used as, for example, a dissociation agent for an adhered cell population.

In a particularly preferable embodiment, the inhibitor of the present invention can be used in maintaining an undifferentiated state of pluripotent stem cells because it efficiently removes deviated cells that develop accidentally during the process of maintenance and expansion of pluripotent cells and/or suppresses the development. HA complex proteins added to the medium are absorbed into cells by endocytosis and the like, decomposed and removed. The HA complex protein of the present invention having a miniaturized molecular size is considered to be more efficiently absorbed and removed by cells than conventional products. In addition, suspension culture of iPS cells in the presence of the HA complex protein of the present invention permits efficient division of iPS cell clump, and efficient amplification of a large amount of iPS cells. The detail of these methods is described in the above-mentioned patent documents 1 and 2.

When the inhibitor of the present invention is used as a dissociation agent for an adhered cell population, it can be performed by adding the inhibitor to a medium for the cell population. The amount of the inhibitor of the present invention to be added to the medium is not particularly limited as long as the cell-cell adhesion in the target cell population is inhibited and the adhered cells can be dissociated. For example, when linked-mini(2+3)/CB-LD/YFDY is added as an HA complex protein to a maintenance culture system of iPS cells, for example, it can be added to the medium at a concentration of not less than 25 nM, preferably not less than 50 nM, more preferably not less than 100 nM. The upper limit of the addition concentration is not particularly set as long as it does not adversely influence the cell survival. It is, for example, not more than 1 µM, preferably not more than 500 nM. The period of addition of the inhibitor of the present invention to the medium is not particularly limited as long as the cell-cell adhesion in the target cell population is inhibited, the adhered cells can be dissociated, and the cell survival is not adversely influenced. It is, for example, 6-72 hr, preferably 12-48 hr, more preferably 24±6 hr. The cell population can be cultured under culture conditions known per se and suitable for the target cells.

The HA complex protein of the present invention is low toxic, does not show an adverse influence on the cell survival, and rather has a cell proliferation promoting action. Therefore, the present invention also provides a cell proliferation promoter containing the HA complex protein of the present invention (hereinafter to be also referred to as "the proliferation promoter of the present invention").

The proliferation promoter of the present invention can be used by adding the medicament to a medium for the cell of interest. The amount of the proliferation promoter of the present invention to be added to the medium is not particularly limited as long as it can significantly increases the proliferation of the cell of interest. For example, when linked-mini(2+3)/CB-LD/YFDY is added as an HA complex protein to a culture system of MDCK cells, for example, it can be added to the medium at a concentration of not less than 25 nM, preferably not less than 50 nM, more preferably not less than 100 nM. The upper limit of the addition concentration is not particularly set as long as it does not adversely influence the cell survival. It is, for example, not more than 1 µM, preferably not more than 500 nM. The period of addition of the proliferation promoter of the present invention to the medium is not particularly limited as long as the proliferation of the cell of interest is significantly increased and the cell survival is not adversely influenced. It is, for example, 6-168 hr, preferably 12-120 hr, more preferably 24-96 hr. The cells can be cultured under culture conditions known per se and suitable for the target cells.

The present invention is explained in more detail in the following by referring to Examples; however, the present invention is not limited to the Examples.

Example

[Materials and Methods]
(1) Production of Plasmid
(I) Alteration of pET52b+(pET52b-C)
The following primers were inserted into the NcoI-SalI site of pET52b+[Novagen].

```
C-strep-f (SEQ ID NO: 14):
taccatggctagcgcaagctacggatccggtagtgcatggagccaccgc
agttcgaaaagtaagtcgacgc C-strep-r (SEQ ID NO: 15):
gcgtcgacttacttttcgaactgcgggtggctccatgcactaccggatcc
gtagcttgcgctagccatggta
```

(II) FL-HA/B(FL-HA of type B)
His-BHA1-Flag (7-294 a.a)
His-BHA2 (2-146 a.a.)
Strep-BHA3 (19-626 a.a.)
Amplification was performed by the PCR method using genomic DNA of *Clostridium botulinum* B-okra strain as a template and the following primers.

```
HA1/B-f (SEQ ID NO: 16):
ctagctagcatccaaaattcattaaatgac

HA1/B-r (SEQ ID NO: 17):
cgggatccttacttgtcgtcatcgtctttgtagtctgggttactcatagt
ccatatc HA2/B-f (SEQ ID NO: 18):
ctagctagctcagctgaaagaacttttctac HA2/B-r (SEQ ID NO: 19):
ccgctcgagttatattttttcaagtttgaacatttg HA3/B-f (SEQ ID NO: 20):
gaaaaagggtaccaatatagtgatactattg HA3/B-r (SEQ ID NO: 21):
cgtgtcgacttaattagtaatatctatatgc
```

HA1 was inserted into the NheI-BamHI site of pET28b+ (Novagen), HA2 was inserted into the NheI-XhoI site of pET28b+(Novagen), and HA3 was inserted into the Kpn-SalI site of pET52b+(Novagen).

(III) N-FL-HA(2+3)/B (FL(2+3) of B Type with Strep Tag Added to the N-Terminal of HA3)
His-BHA2 (2-146 a.a.)
Strep-BHA3 (19-626 a.a.)
Amplification was performed by the PCR method using genomic DNA of *Clostridium botulinum* B-okra strain as a template and the following primers.

```
HA2/B-f (SEQ ID NO: 18):
ctagctagctcagctgaaagaacttttctac

HA2/B-r (SEQ ID NO: 19):
ccgctcgagttatattttttcaagtttgaacatttg

HA3/B-f (SEQ ID NO: 20):
gaaaaagggtaccaatatagtgatactattg

HA3/B-r (SEQ ID NO: 21):
cgtgtcgacttaattagtaatatctatatgc
```

HA2 was inserted into NheI-XhoI site of pET28b+(Novagen), and HA3 was inserted into KpnI-SalI site of pET52b+ (Novagen).

(IV) C-FL-HA(2+3)/B (FL(2+3) of B Type with Strep Tag Added to the C-Terminal of HA3)

His-BHA2 (2-146 a.a.)
BHA3-Strep (19-626 a.a.)

Amplification was performed by the PCR method using genomic DNA of *Clostridium botulinum* B-okra strain as a template and the following primers.

```
HA2/B-f (SEQ ID NO: 18):
ctagctagctcagctgaaagaacttttctac

HA2/B-r (SEQ ID NO: 19):
ccgctcgagttatattttttcaagtttgaacatttg

HA3/B-f (SEQ ID NO: 22):
gcgctagcaatatagtgatactattgatttagctgatgg

HA3/B-r (SEQ ID NO: 23):
ccggatccattagtaatatctatatgcaattttatattatag
```

HA2 was inserted into NheI-XhoI site of pET28b+(Novagen), and HA3 was inserted into NheI-BamHI site of pET52b-C.

(V) Linked-FL-HA(2+3)/B(Linked-FL(2+3) of Type B)

BHA3-linker-BHA2-Strep (19-626 a.a+1-9 a.a.+2-146 a.a.)

Amplification was performed by the PCR method using pET28b-BHA2 and pET52b-BHA3 as templates and the following primers.

```
HA2/B-f (SEQ ID NO: 24):
ggggtgatgaccctccaggatcagctgaaagaacttttctacctaatg

HA2/B-r (SEQ ID NO: 25):
actaccggatcctatttttttcaagtttgaacatttg

HA3/B-f (SEQ ID NO: 26):
taagaaggagatataccatggctagc

HA3/B-r (SEQ ID NO: 27):
gggtcatcaccccacttccattagtaatatctatatgcaattttatattata
```

HA2 and HA3 were inserted into NcoI-BamHI site of pET52b-C by using GeneArt (registered trade mark) Seamless Cloning and Assembly Kit (Invitrogen).

(VI) Mini-HA/B(Mini-HA of Type B)

His-BHA1-FLAG (7-294 a.a)
His-BHA2 (2-146 a.a.)
BHA3mini-Strep (380-626 a.a.)

Amplification was performed by the PCR method using genomic DNA of *Clostridium botulinum* B-okra strain as a template and the following primers.

```
HA1/B-f (SEQ ID NO: 16):
ctagctagcatccaaaattcattaaatgac

HA1/B-r (SEQ ID NO: 17):
cgggatccttacttgtcgtcatcgtctttgtagtctgggttactcatagt
ccatatc HA2/B-f (SEQ ID NO: 18):
ctagctagctcagctgaaagaacttttctac HA2/B-r (SEQ ID NO: 19):
ccgctcgagttatattttttcaagtttgaacatttg HA3mini/B-f (SEQ ID NO: 28):
gcgctagcgaaaatatacaagaaataaatactgctatttcag HA3mini/B-r (SEQ ID NO: 23):
ccggatccattagtaatatctatatgcaattttatattatag
```

HA1 was inserted into NheI-BamHI site of pET28b+ (Novagen), HA2 was inserted into NheI-XhoI site of pET28b+(Novagen), and HA3mini was inserted into NheI-BamHI site of pET52b-C.

(VII) Mini-HA(2+3)/B(Mini(2+3) of Type B)

His-BHA2 (2-146 a.a.)
BHA3mini-Strep (380-626 a.a.)

Amplification was performed by the PCR method using genomic DNA of *Clostridium botulinum* B-okra strain as a template and the following primers.

```
HA2/B-f (SEQ ID NO: 18):
ctagctagctcagctgaaagaacttttctac

HA2/B-r (SEQ ID NO: 19):
ccgctcgagttatattttttcaagtttgaacatttg

HA3mini/B-f (SEQ ID NO: 28):
gcgctagcgaaaatatacaagaaataaatactgctatttcag

HA3mini/B-r (SEQ ID NO: 23):
ccggatccattagtaatatctatatgcaattttatattatag
```

HA2 was inserted into NheI-XhoI site of pET28b+(Novagen), and HA3mini was inserted into NheI-BamHI site of pET52b-C.

(VIII) Mini-HA(2+3)/CB(Mini(2+3)/CB)

His-CHA2 (2-146 a.a.)
BHA3mini-Strep (380-626 a.a.)

Amplification was performed by the PCR method using genomic DNAs of *Clostridium botulinum* C-st strain, B-okra strain as templates and the following primers.

```
HA2/C-f (SEQ ID NO: 29):
ctagctagctcaagtgaaagaaccttttac

HA2/C-r (SEQ ID NO: 30):
acgcgtcgacttaaagttttctaattttaaaatttg

HA3mini/B-f (SEQ ID NO: 28):
gcgctagcgaaaatatacaagaaataaatactgctatttcag

HA3mini/B-r (SEQ ID NO: 23):
ccggatccattagtaatatctatatgcaattttatattatag
```

HA2 was inserted into NheI-SalI site of pET28b+(Novagen), and HA3mini was inserted into NheI-BamHI site of pET52b-C.

(IX) Linked-Mini-HA(2+3)/B(Linked-Mini(2+3)/BB)

BHA3mini-linker-BHA2-Strep (380-626 a.a+1-9 a.a.+2-146 a.a.)

Amplification was performed by the PCR method using pET28b-BHA2 and pET52b-BHA3 as templates and the following primers.

HA2/B-f (SEQ ID NO: 24):
ggggtgatgaccctccaggatcagctgaaagaacttttctacctaatg

HA2/B-r (SEQ ID NO: 25):
actaccggatcctattttttcaagttgaacatttg

HA3mini/B-f (SEQ ID NO: 26):
taagaaggagatataccatggctagc

HA3mini/B-r (SEQ ID NO: 27):
gggtcatcacccccacttccattagtaatatctatatgcaattttatattata HA2 and HA3mini were inserted into NcoI-BamHI site of pET52b-C by using GeneArt (registered trade mark) Seamless Cloning and Assembly Kit (Invitrogen).

(X) Linked-Mini-HA(2+3)/CB(Linked-Mini(2+3)/CB)

BHA3mini-linker-CHA2-Strep (380-626 a.a+1-9 a.a.+2-146 a.a.)

Amplification was performed by the PCR method using pET28b-CHA2 and pET52b-BHA3 as templates and the following primers.

```
HA2/C-f (SEQ ID NO: 31):
ggggtgatgaccctccaggatcaagtgaaagaacctttttacctaatg

HA2/C-r (SEQ ID NO: 32):
actaccggatccaagttttctaattttaaaatttgattag

HA3mini/B-f (SEQ ID NO: 26):
taagaaggagatataccatggctagc

HA3mini/B-r (SEQ ID NO: 27):
gggtcatcacccccacttccattagtaatatctatatgcaattttatatt
ata
```

HA2 and HA3mini were inserted into NcoI-BamHI site of pET52b-C by using GeneArt (registered trade mark) Seamless Cloning and Assembly Kit (Invitrogen).

(XI) Linked-Mini-HA(2+3)/CB-YFDY(Linked-Mini(2+3)/CB-YFDY)

HA2-Y73D-F75Y

Mutation was introduced by the site-directed mutagenesis method using pET52b-C-linked-mini-HA(2+3)/CB as a template and the following primers.

```
Y73D/F75Y-f (SEQ ID NO: 33):
atgatgatggttatatctatttaagttcatcatctaataatag

Y73D/F75Y-r (SEQ ID NO: 34):
agatataaccatcatcattataagctaaatatttattagg
```

(XII) Linked-Mini-HA(2+3)/CB-IC(Linked-Mini(2+3)/CB-IC)

HA2-Y73D-F75Y-I90C

Mutation was introduced by the site-directed mutagenesis method using pET52b-C-linked-mini-HA(2+3)/CB-YFDY as a template and the following primers.

```
I90C-f (SEQ ID NO: 35):
aatccttgtaaaattgctataaattcttatattatatg

I90C-r (SEQ ID NO: 36):
aattttacaaggattccataaactattattag
```

(XIII) Linked-Mini-HA(2+3)/CB-ITCC(Linked-Mini(2+3)/CB-ITCC)

HA2-Y73D-F75Y-I90C, HA3-T572C

Mutation was introduced by the site-directed mutagenesis method using pET52b-C-linked-mini-HA(2+3)/CB-YFDY-IC as a template and the following primers.

```
T572C-f (SEQ ID NO: 37):
agagtctgtgaaactattgacggctataattt

T572C-r (SEQ ID NO: 38):
agtttcacagactctaaataaagtacctattc
```

(XIV) Linked-Mini-HA(2+3)/CB-YFDY-LD(Linked-Mini(2+3)/CB-LD/YFDY)

HA2-L40D-Y73D-F75Y

Mutation was introduced by the site-directed mutagenesis method using pET52b-C-linked-mini-HA(2+3)/CB-YFDY as a template and the following primers.

```
L40D-f (SEQ ID NO: 39):
tcttctgatgataatcaaaaatggaagttag

L40D-r (SEQ ID NO: 40):
attatcatcagaagatgtatttgaaaatgataatg
```

(2) Protein Expression

The plasmids produced above were transformed into Rosetta2 (DE3) [Novagen]. Protein expression was induced using Overnight Express Autoinduction System 1 [Novagen]. After induction of expression of each plasmid as follows, *Escherichia coli* was collected by centrifugation and preserved at −80° C. until use.

pET28b-BHA1 . . . 18° C., 48 hr
pET28b-BHA2 . . . 18° C., 48 hr
pET28b-CHA2 . . . 18° C., 48 hr
pET52b-BHA3 . . . 30° C., 36 hr
pET52b-C-BHA3 . . . 30° C., 36 hr
pET52b-C-BHA3mini . . . 30° C., 36 hr
pET52b-C-linked-mini-HA(2+3)/B . . . 30° C., 20 hr
pET52b-C-linked-mini-HA(2+3)/CB . . . 30° C., 20 hr Performed for each variant under the same conditions as for the wild-type.

(3) Protein Purification

Respective proteins were purified using the following.

pET28b-BHA1 . . . His-Trap HP [GE Healthcare]
pET28b-BHA2 . . . His-Trap HP [GE Healthcare]
pET28b-CHA2 . . . His-Trap HP [GE Healthcare]
pET52b-BHA3 . . . Strep-Trap HP [GE Healthcare]
pET52b-C-BHA3 . . . Strep-Trap HP [GE Healthcare]
pET52b-C-BHA3mini . . . Strep-Trap HP [GE Healthcare]
pET52b-C-linked-mini-HA(2+3)/B . . . Strep-Trap HP [GE Healthcare]
pET52b-C-linked-mini-HA(2+3)/CB . . . Strep-Trap HP [GE Healthcare]

In the complexes (II, III, IV, VI, VII, VIII), they were mixed at a molar ratio of (HA1:)HA2:HA3=(4:)4:1, incubated at 37° C. for 3 hr, and purified using Strep-Trap HP [GE Healthcare].

(4) Protein amino acid sequence (tag (and vector-derived sequence) or linker sequence are/is underlined)

```
>His-BHA1-Flag (SEQ ID NO: 41):
MGSSHHHHHHSSGLVPRGSHMASIQNSLNDKIVTISCKANTDLFFYQVPGNGNVSLFQQTRNY

LERWRIIYDSNKAAYKIKSMNIYNTNLVLTWNAPTHNISAQQDSNADNQYWLLLKDIGNNSFI
```

-continued

IASYKNPNLVLYADTVARNLKLSTLNNSSYIKFIIEDYVISDFKNFTCRISPILAGGKVVQQV
SMTNLAVNLYIWNNDLNQKWTIIYNEEKAAYQFFNKILSNGVLTWIFSDGNTVRVSSSAQNND
AQYWLINPVSDNYDRYTITNLRDKTKVLDLYGGQTADGTTIQVFNSNGGDNQIWTMSNPDYKD
DDDK

>His-BHA2 (SEQ ID NO: 42):
MGSSHHHHHHSSGLVPRGSHMASSAERTFLPNGNYNIKSIFSGSLYLSPVSGSLTESNESSAN
NQKWNVEYMAENRCFKISNVAEPNKYLSYDNEGFISLDSLSNRCYWFPIKIAVNTYIMLSLNK
VNELDYAWDIYDTNENILSQPLLLLPNFDIYNSNQMFKLEKI

>Strep-BHA3 (SEQ ID NO: 43):
MASWSHPQFEKGALEVLFQGPGYQYSDTIDLADGNYVVSRGDGWILSRQNQILGGSVISNGST
GIVGDLRVNDNAIPYYYPTPSFNEEYIKNNIQTVFANFTEANQIPIGFEFSKTAPSNKNLYMY
LQYTYIRYEIIKVLQHEIIERAVLYVPSLGYVKSIEFNPGEKINKDFYFLTNDKCILNEQFLY
KKILETTKNIPTNNIFNSKVSSTQRVLPYSNGLYVINKGDGYIRTNDKDLIGTLLIEAGSSGS
IIQPRLRNTTRPLFTTSNDAKFSQQYTEERLKDAFNVQLFNTSTSLFKFVEEAPSNKNICIKA
YNTYEKYELIDYQNGSIVNKAEYYLPSLGYCEVTNAPSPESEVVKTQVAEDGFIQNGPEEEIV
VGVIDPSENIQEINTAISDNYTYNIPGIVNNNPFYILFTVNTTGIYKINAQNNLPSLKIYEAI
GSGNRNFQSGNLCDDDIKAINYITGFDSPNAKSYLVVLLNKDKNYYIRVPQTSSNIENQIKFK
REEGDLRNLMNSSVNIIDNLNSTGAHYYTRQSPDVHDYISYEFTIPGNFNNKDTSNIRLYTSY
NQGIGTLFRVTETIDGYNLINIQQNLNLLNSTKSIRLLNGAIYILKVEVTELNNYNIKLHIDI
TN >BHA3-Strep (SEQ ID NO: 44):
MASYSDTIDLADGNYVVSRGDGWILSRQNQILGGSVISNGSTGIVGDLRVNDNAIPYYYPTPS
FNEEYIKNNIQTVFANFTEANQIPIGFEFSKTAPSNKNLYMYLQYTYIRYEIIKVLQHEIIER
AVLYVPSLGYVKSIEFNPGEKINKDFYFLTNDKCILNEQFLYKKILETTKNIPTNNIENSKVS
STQRVLPYSNGLYVINKGDGYIRTNDKDLIGTLLIEAGSSGSIIQPRLRNTTRPLFTTSNDAK
FSQQYTEERLKDAFNVQLFNTSTSLFKFVEEAPSNKNICIKAYNTYEKYELIDYQNGSIVNKA
EYYLPSLGYCEVTNAPSPESEVVKTQVAEDGFIQNGPEEEIVVGVIDPSENIQEINTAISDNY
TYNIPGIVNNNPFYILFTVNTTGIYKINAQNNLPSLKIYEAIGSGNRNFQSGNLCDDDIKAIN
YITGFDSPNAKSYLVVLLNKDKNYYIRVPQTSSNIENQIKFKREEGDLRNLMNSSVNIIDNLN
STGAHYYTRQSPDVHDYISYEFTIPGNFNNKDTSNIRLYTSYNQGIGTLFRVTETIDGYNLIN
IQQNLNLLNSTKSIRLLNGAIYILKVEVTELNNYNIKLHIDITNGSGSAWSHPQFEK >linked-FL(2 + 3)/BB(SEQ ID NO: 45):
MASYSDTIDLADGNYVVSRGDGWILSRQNQILGGSVISNGSTGIVGDLRVNDNAIPYYYPTPS
FNEEYIKNNIQTVFANFTEANQIPIGFEFSKTAPSNKNLYMYLQYTYIRYEIIKVLQHEIIER
AVLYVPSLGYVKSIEFNPGEKINKDFYFLTNDKCILNEQFLYKKILETTKNIPTNNIFNSKVS
STQRVLPYSNGLYVINKGDGYIRTNDKDLIGTLLIEAGSSGSIIQPRLRNTTRPLFTTSNDAK
FSQQYTEERLKDAFNVQLFNTSTSLFKFVEEAPSNKNICIKAYNTYEKYELIDYQNGSIVNKA
EYYLPSLGYCEVTNAPSPESEVVKTQVAEDGFIQNGPEEEIVVGVIDPSENIQEINTAISDNY
TYNIPGIVNNNPFYILFTVNTTGIYKINAQNNLPSLKIYBAIGSGNRNFQSGNLCDDDIKAIN
YITGFDSPNAKSYLVVLLNKDKNYYIRVPQTSSNIENQIKFKREEGDLRNLMNSSVNIIDNLN
STGAHYYTRQSPDVHDYISYEFTIPGNFNNKDTSNIRLYTSYNQGIGTLFRVTETIDGYNLIN
IQQNLNLLNSTKSIRLLNGAIYILKVEVTELNNYNIKLHIDITNGSGGDDPPGSAERTFLPNG

NYNIKSIFSGSLYLSPVSGSLTFSNESSANNQKWNVEYMAENRCFKISNVAEPNKYLSYDNPG

FISLDSLSNRCYWFPIKIAVNTYIMLSLNKVNELDYAWDIYDTNENILSQPLLLLPNFDIYNS

NQMFKLEKIGSGSAWSHPQFEK

>BHA3mini-Strep (SEQ ID NO: 46):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVTETIDGYNLINIQQNLNLLNSTKSIRLLNGAIYILKVEVTELNNYNIKLHIDITNGS

GSAWSHPQFEK

>linked-mini(2 + 3)/BB (SEQ ID NO: 47):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVTETIDGYNLINIQQNLNLINSTKSIRLLNGAIYILKVEVTELNNYNIKLHIDITNGS

GGDDPPGSAERTFLPNGNYNIKSIFSGSLYLSPVSGSLTFSNESSANNQKWNVEYMAENRCFK

ISNVAEPNKYLSYDNFGFISLDSLSNRCYWFPIKIAVNTYIMLSLNKVNELDYAWDIYDTNEN

ILSQPLLLLPNFDIYNSNQMFKLEKIGSGSAWSHPQFEK

>linked-mini (2 + 3)/CB (SEQ ID NO: 48):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNICTSNIRLYTSYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDYGFIYLSSSSNNSLWNPIKIAINSYIICTLSIVNVTDYAWTIYDNNNN

ITDQPILNLPNFDINNSNQILKLEKLGSGSAWSHPQFEK

>linked-mini (2 + 3)/CB-YFDY (SEQ ID NO: 49):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDDGYIYLSSSSNNSLWNPIKIAINSYIICTLSIVNVTDYAWTIYDNNNN

ITDQPILNLPNFDINNSNQILKLEKLGSGSAWSHPQFEK

>linked-mini (2 + 3)/CB-LD/YFDY (SEQ ID NO: 50):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSDDNQKWKLEYISSSNGFR

FSNVAEPNKYLAYNDDGYIYLSSSSNNSLWNPIKIAINSYIICTLSIVNVTDYAWTIYDNNNN

ITDQPILNLPNFDINNSNQILKLEKLGSGSAWSHPQFEK

>linked-mini (2 + 3)/CB-YFDY/IC (SEQ ID NO: 51):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

-continued

DLRNLMNSSVNIIDNLNSTGAHYYTRQSPDVHDYISYEFTIPGNFNNKDTSNIRLYISYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDDGYIYLSSSSNNSLWNPCKIAINSYTICTLSIVNVTDYAWTIYDNNNN

ITDQPILNLPNEDINNSNQILKLEKLGSGSAWSHPQFEK

>linked-mini (2 + 3)/CB-YFDY/ITCC (SEQ ID NO: 52):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVCETIDGYNLINIQQNLNLLNSTKSIRLINGAIYILKVEVIELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDDGYIYLSSSSNNSLWNPCKIAINSYIICTLSIVNVIDYAWTIYDNNNN

ITDQPILNLPNFDINNSNQLKLEKLGSGSAWSHPQFEK (5) TER Test
1. Caco-2 cells were seeded in a collagen-coated transwell chamber with 0.4 µm-pore size 6.5 mm diameter [Costar], and cultured in Caco-2 cell culture medium (20% FBS [Equitech-Bio], MEM [Gibco], 1 mM L-glutamine [Gibco], 17.86 mM NaHCO$_3$ [Wako], 15 mM Hepes [Dojindo], pH 7.4, 70 U/ml penicillin G-70 µg/ml Streptomycin [Gibco]) in a CO$_2$ incubator (37° C., 5% CO$_2$).
2. The medium was changed every 3 days until the TER value reached 600 Ω·cm$^2$ or more.
3. Each transwell was washed with PBS the day before the test, and the cells were cultured overnight in the medium in a CO$_2$ incubator.
4. Each HA was added to 2 or 3 wells and to the basal side chamber of each well to a final concentration of 30-300 nM by protomer calculation, and cultured in a CO$_2$ incubator.
5. Until 24 hr after HA addition, the TER value of each well was measured over time using Millicell-ERS2 [Millipore].
6. The measurement values were calculated by the following formula, the mean of 2 or 3 wells was determined, and the standard deviation was taken as the error.

$$[TER^{calc(X\,hr)}] = ([TER^{X\,hr}]/[TER^{0\,hr}]) \times 100$$

(6) Cytotoxicity Test
1. Caco-2 cells were seeded on a 96 well plate at 1×10^4 cell/well in a Caco-2 cell culture medium (100 µl/well), and cultured in a CO$_2$ incubator (37° C., 5% CO$_2$) for 24 hr.
2. A well containing a medium alone and without seeding of cells was used as a blank.
3. 1% Triton X-100 or various proteins were added to 3 wells each of a 96 well plate to a final concentration of 300 nM by protomer calculation, and cultured in a CO$_2$ incubator for 48 hr.
4. SF reagent [nacalai tesque] was added by 10 µl to each well, followed by culture for 1.5 hr.
5. 1% SDS was added by 10 µl to each well, and absorbance was measured at wavelength 450 nm and 620 nm.
6. The measurement values were calculated by the following formula.

$$A450^{calc(sample)} = ([A450^{sample}] - [A620^{sample}]) - ([A450^{blank}] - [A620^{blank}])$$

7. As the measurement value, an average of 3 wells was determined under respective conditions and standard deviation was taken as the error.

(7) Cell-Cell Adhesion Inhibitory Test
1. Human iPS cell D2 strain (obtained from: Center for iPS Cell Research and Application (CiRA), Kyoto University) precultured for 4 days on a 100 mm dish was seeded under feeder-free conditions at a density of 2.5×10$^3$ cells/cm$^2$ in a 48-well plate (costar 3548) with each well containing Stem-Fit (registered trade mark) AK02N medium (200 µl) (Day0).
2. The 48-well plate was cultured in a CO$_2$ incubator at 5% CO$_2$ atmosphere at 37° C. for 3 days. The medium was changed every other day, various concentrations (0.1-450 nM) of linked-mini(2+3)/CB-LD/YFDY or FL-HA(HFHS) of type B were added to the wells (each concentration 2 wells) for 24 hr from the day of start of culture (Day1) to 2 days (Day2). On 1, 2 and 3 days from the start of culture, microscopic photograph (4×) was taken.
(8) Cell Proliferation Test
(a) SF Assay
1. MDCK cells were seeded on a 96 well plate at 1×10$^4$ cells/well in a MDCK cell culture medium (100 µl/well), and cultured in a CO$_2$ incubator (37° C., 5% CO$_2$) for 24 hr.
2. FL-HA or linked-mini (2+3)/CB-LD/YFDY was added to 3 wells each of a 96 well plate to a final concentration of 1-300 nM, and cultured in a CO$_2$ incubator for 24 hr.
3. SF reagent [nacalai tesque] was added by 10 µl to each well, followed by culture in a CO$_2$ incubator for 1.5 hr.
4. 1% SDS was added by 10 µl to each well, and absorbance was measured at wavelength 450 nm and 620 nm.
5. The measurement values were calculated by the following formula.

$$A450^{calc(sample)} = ([A450^{sample}] - [A620^{sample}]) - ([A450^{blank}] - [A620^{blank}])$$

Figure 2:
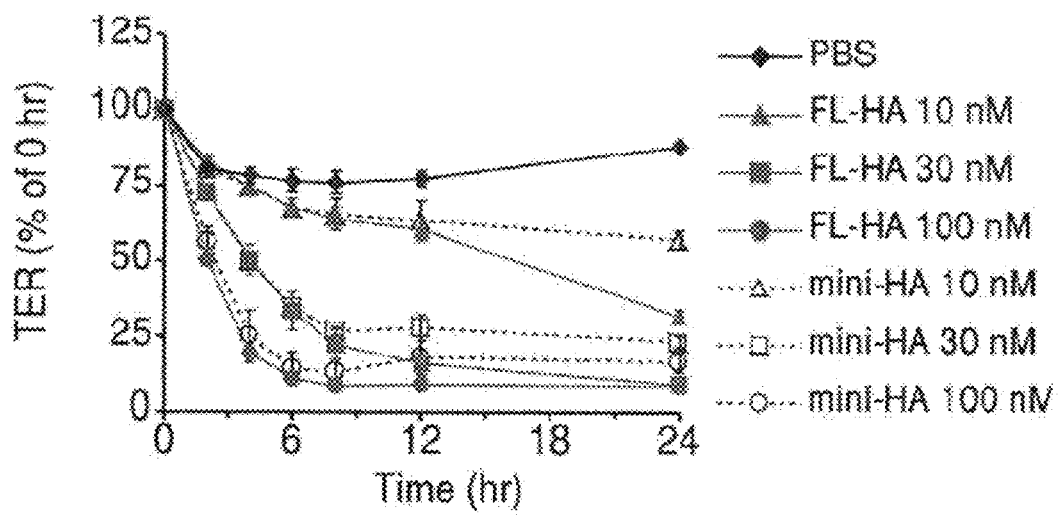
FIG. 2 is a drawing showing the effects of a mini-HA complex and a FL-HA complex on the TER value in cultured Caco-2 cells.
Figure 3:
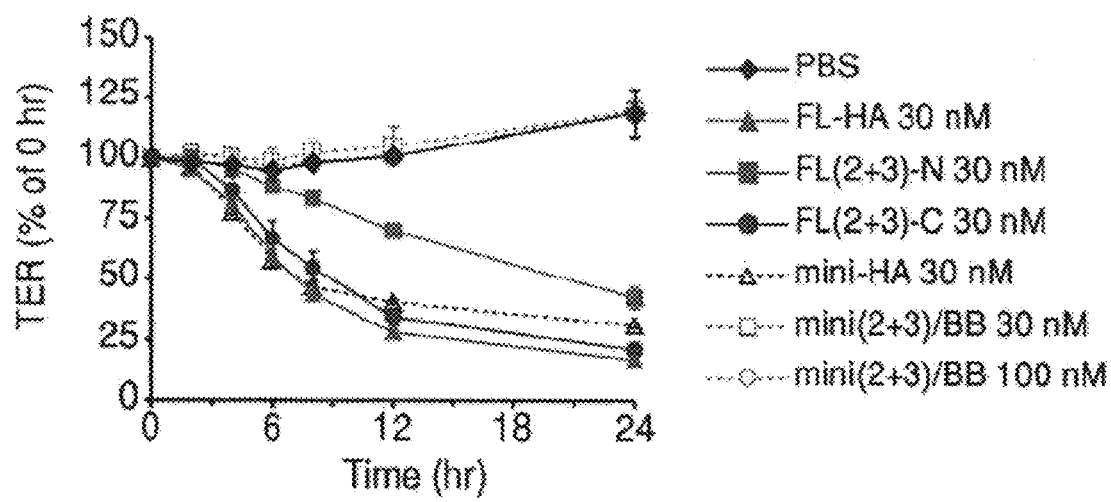
FIG. 3 is a drawing showing the effects of a mini (2+3) complex and a FL (2+3)-N and FL (2+3)-C complex on the TER value in cultured Caco-2 cells.
Figure 4:
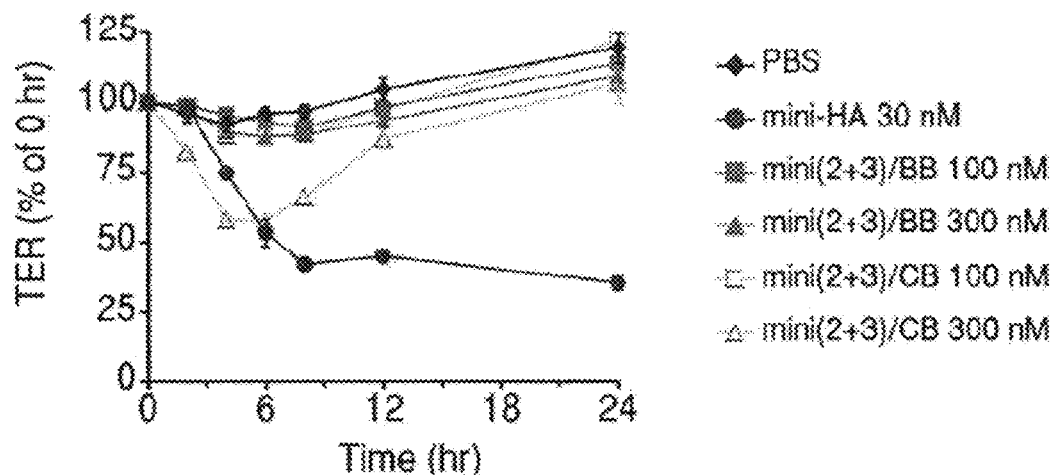
FIG. 4 is a drawing showing the effects of a mini (2+3)/BB complex and a mini (2+3)/CB complex on the TER value in cultured Caco-2 cells.
Figure 5:
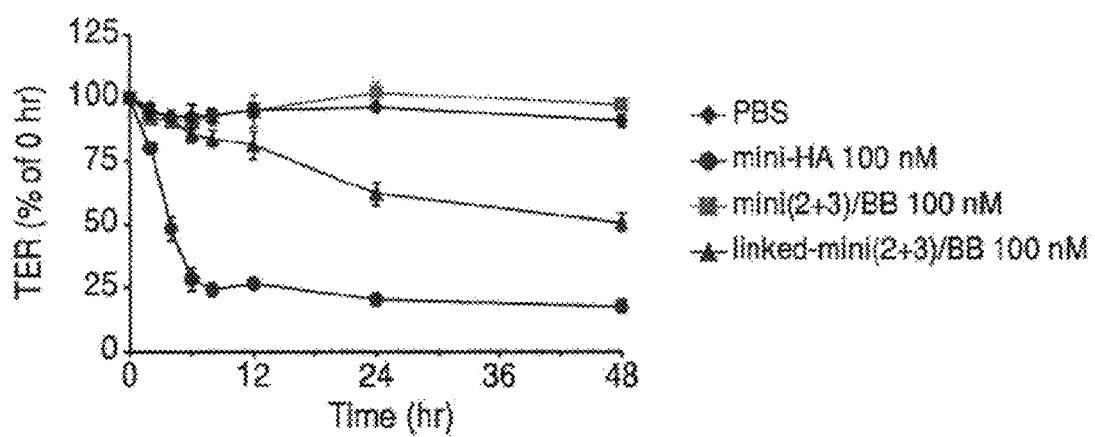
FIG. 5 is a drawing showing the effects of a mini (2+3)/BB complex and a linked-mini (2+3)/BB complex on the TER value in cultured Caco-2 cells.
Figure 12:
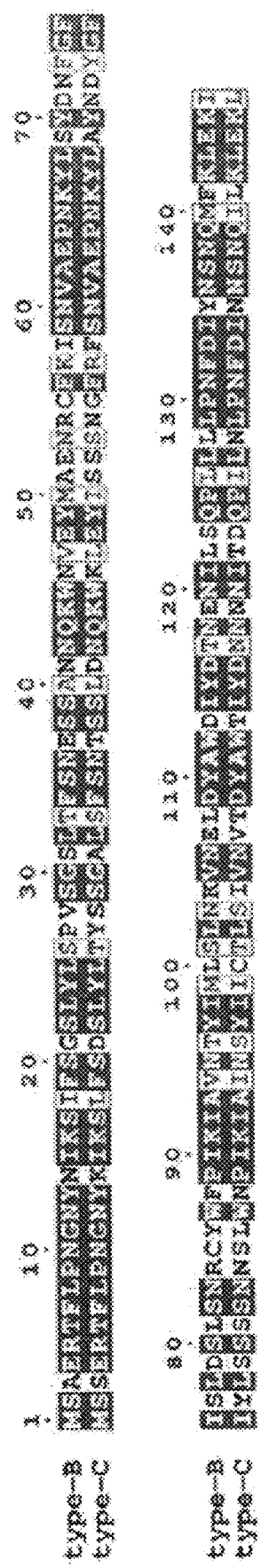
FIG. 12 is a drawing showing alignment of HA2 subcomponents of type B (SEQ ID NO: 4) and type C (SEQ ID NO: 5).

6. As the measurement value, an average of 3 wells was determined under respective conditions and standard deviation was taken as the error.
(b) Cell Number Measurement
1. MDCK cells were seeded on a 35 mm dish in an MDCK cell culture medium (1.5 ml/dish) at 1×10 cells/dish, and cultured in a CO$_2$ incubator (37° C., 5% CO$_2$) for 48 hr.
2. Each dish was washed with PBS, FL-HA at final concentration of 30 nM (protomer 90 nM) or linked-mini (2+3)/CB-LD/YFDY at a final concentration of 100 nM was added to 3 dishes each, and cultured in a CO$_2$ incubator for 48 hr.
3. Each dish was washed with PBS, 0.25% trypsin-EDTA [GIBCO] was added to the dish, of the dish was incubated in a CO$_2$ incubator for 30 min. Then, an FBS-containing medium was added to each dish and the cells were collected.
4. The number of cells was counted using a ceil counter [One Cell].
5. As the number of cells, the average of 3 dishes was calculated in each group, and the standard deviation was taken as the error.
[Results]
(1) The effects of various concentrations of whole HA 12-mer (FL-HA) and a monovalent HA complex lacking a part of HA3 (mini-HA) on the TER value of Caco-2 cells were examined. As a result, it was shown that mini-HA has cadherin function inhibitory activity similar to that of FL-HA (FIG. 2).
(2) The effects of various concentrations of trivalent, C-terminal or N-terminal-tagged complexes lacking HA1 subcomponent (FL(2+3)-C, FL(2+3)-N) on the TER value of Caco-2 cells were examined. As a result, when a tag was added to the N-terminal of the HA3 subcomponent, the cadherin function inhibitory activity decreased to about ⅓ of that of FL-HA. On the other hand, when the tag was added to the C-terminal of HA3 subcomponent, the cadherin function inhibitory activity was maintained at a level near that of FL-HA (FIG. 3).
(3) The effects of various concentrations of mini(2+3) lacking the HA1 subcomponent on the TER value of Caco-2 cells were examined. As a result, mini(2+3) did not have or showed very weak cadherin function inhibitory activity (FIG. 3).
(4) In mini(2+3), the effects of various concentrations (concentration as protomer molecule) of mini(2+3)/CB having the HA2 subcomponent substituted by type C on the TER value of Caco-2 cells were examined (alignment of amino acid sequences HA2 of type B and HA2 of type C is shown in FIG. 12). As a result, it was clarified that cadherin function inhibitory activity was shown, though temporarily, by the use of the HA2 subcomponent of type C (FIG. 4).
(5) When the HA2 subcomponent and the HA3 subcomponent were linked via a linker (FIG. 13), mini(2+3)/BB showed cadherin function inhibitory activity even though the HA2 subcomponent was type B (FIG. 5).

Figure 6:
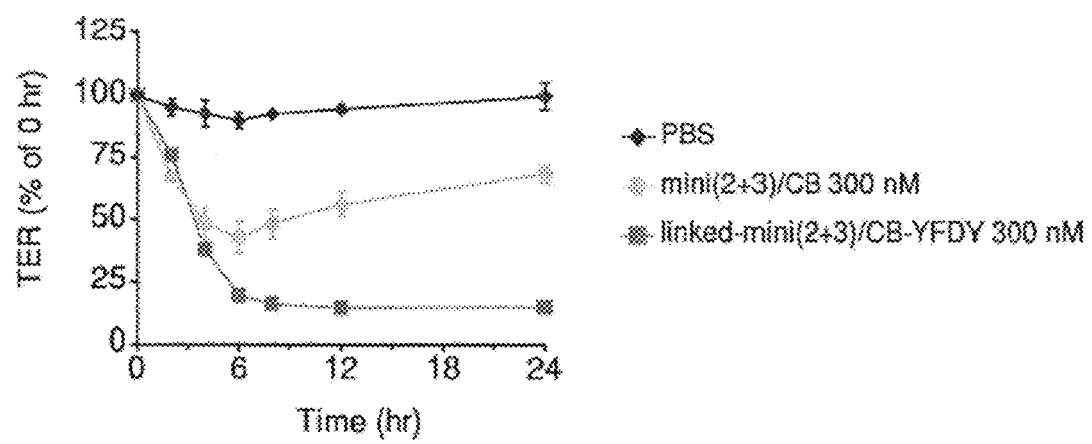
FIG. 6 is a drawing showing the effects of a mini (2+3)/CB complex and a linked-mini (2+3)/CB-YFDY complex on the TER value in cultured Caco-2 cells.
Figure 7:
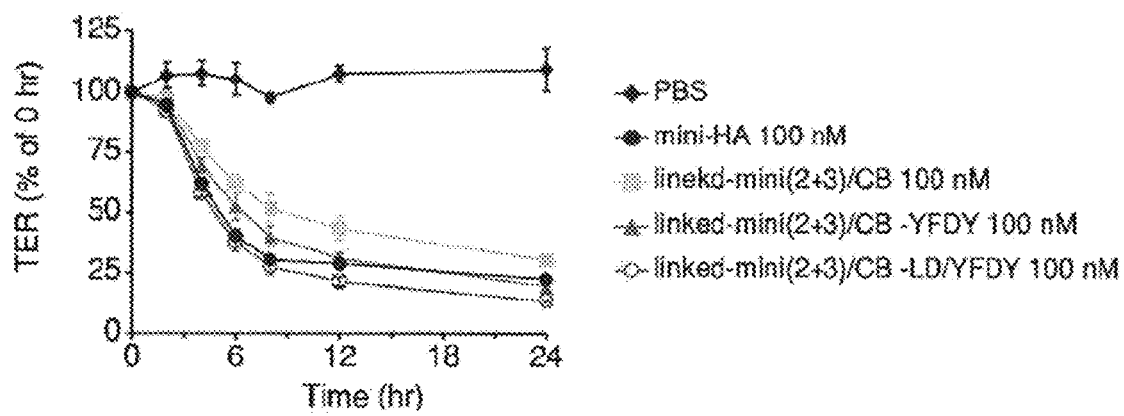
FIG. 7 is a drawing showing the effects of a linked-mini (2+3)/CB complex, a linked-mini (2+3)/CB-YFDY complex and a linked-mini (2+3)/CB-LD/YFDY complex on the TER value in cultured Caco-2 cells.
Figure 11:
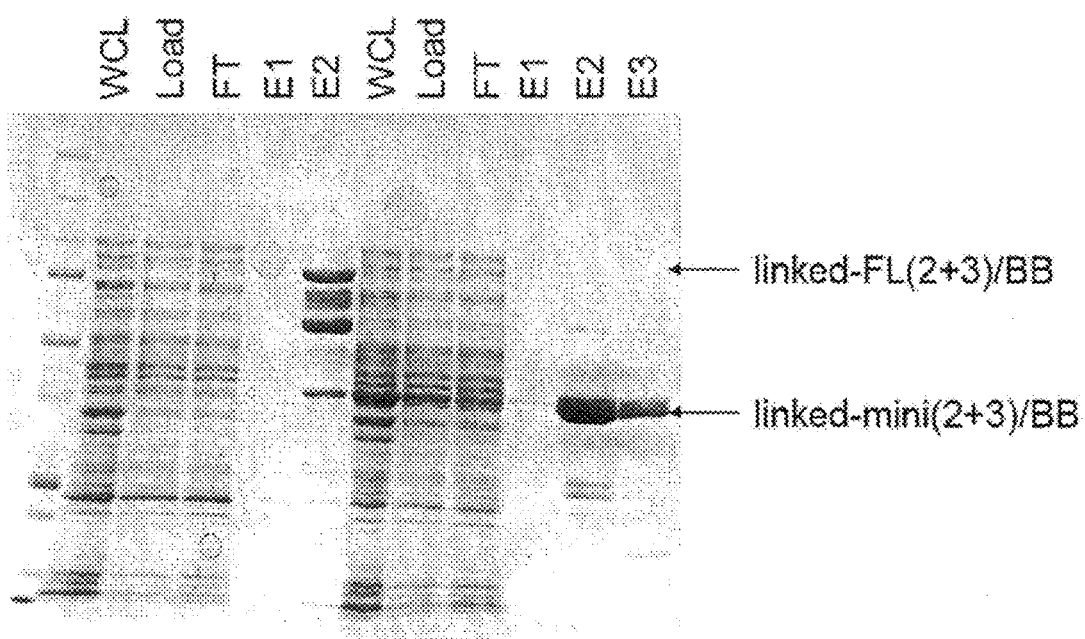
FIG. 11 is a drawing showing a comparison of a linked-mini (2+3) complex and a linked-FL (2+3) complex in the expression and purification.

In mini(2+3)/CB, when the HA2 subcomponent and the HA3 subcomponent were linked via a linker, the cadherin function inhibitory activity changed from temporary to sustained one (FIG. 6, FIG. 7).
(6) In linked-mini(2+3)/CB, various mutations shown in FIGS. 14 and 15 were introduced and change of cadherin function inhibitory activity was examined. As a result, when a mutation that replaces hydrophobic amino acid residues in the HA2 subcomponent with more hydrophilic amino acids was introduced [linked-mini(2+3)/CB-YFDY, linked-mini(2+3)/CB-LD/YFDY], the cadherin function inhibitory activity was further improved and activity equivalent to that of mini-HA was shown (FIG. 7). On the other hand, when a cysteine residue was introduced into each of the HA2 subcomponent and the HA3 subcomponent [linked-mini(2+3)/CB-YFDY/ITCC], the cadherin function inhibitory activity which became persistent with the use of linker changed to temporary one (FIG. 8).
(7) The HA2 subcomponent and the HA3 subcomponent were linked via a linker, a construct with strep tag added to the C-terminal of HA2 was introduced into *Escherichia coli* to allow for expression, and the culture medium was applied to StrepTrap to purify linked-mini(2+3)/BB. As a result, contaminants or decomposed products were often found in linked-FL(2+3)/BB but linked-mini(2+3)/BB could be purified at a high purity (FIG. 11).

Figure 10:
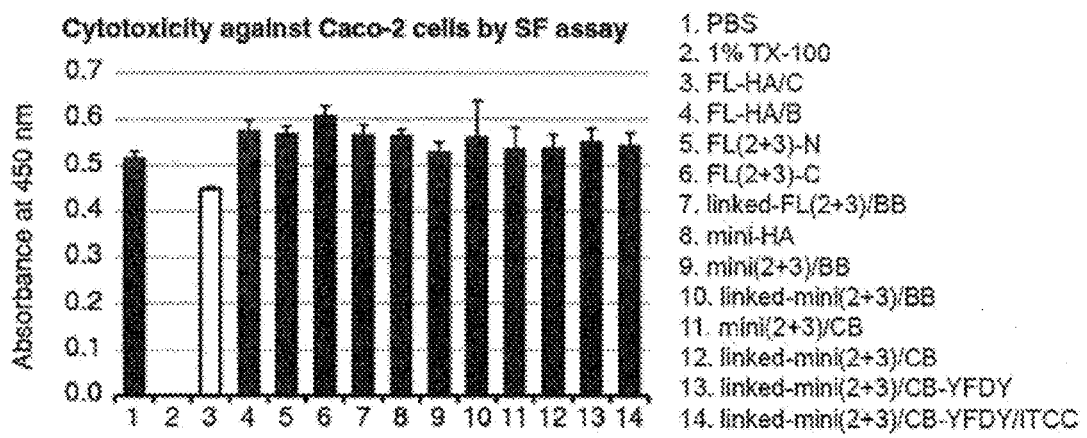
FIG. 10 is a drawing showing the results of a cytotoxicity test of various HA complex proteins against Coca-2 cells.
Figure 16A:
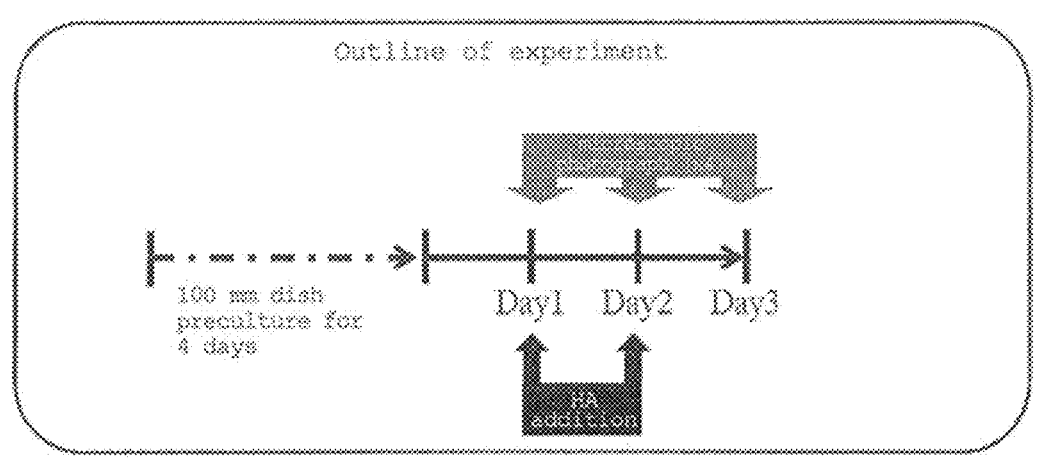
FIGS. 16A and 16B are drawing showing the effects of a linked-mini (2+3)/CB-LD/YFDY complex on the cell-cell adhesion of iPS cells.
Figure 16B:
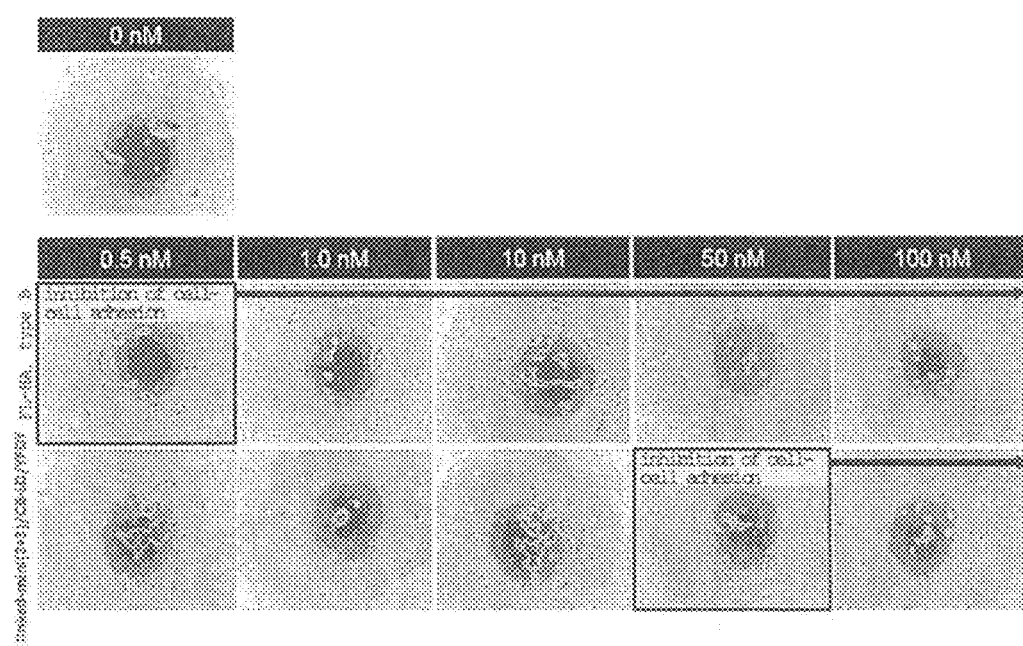
Figure 17:
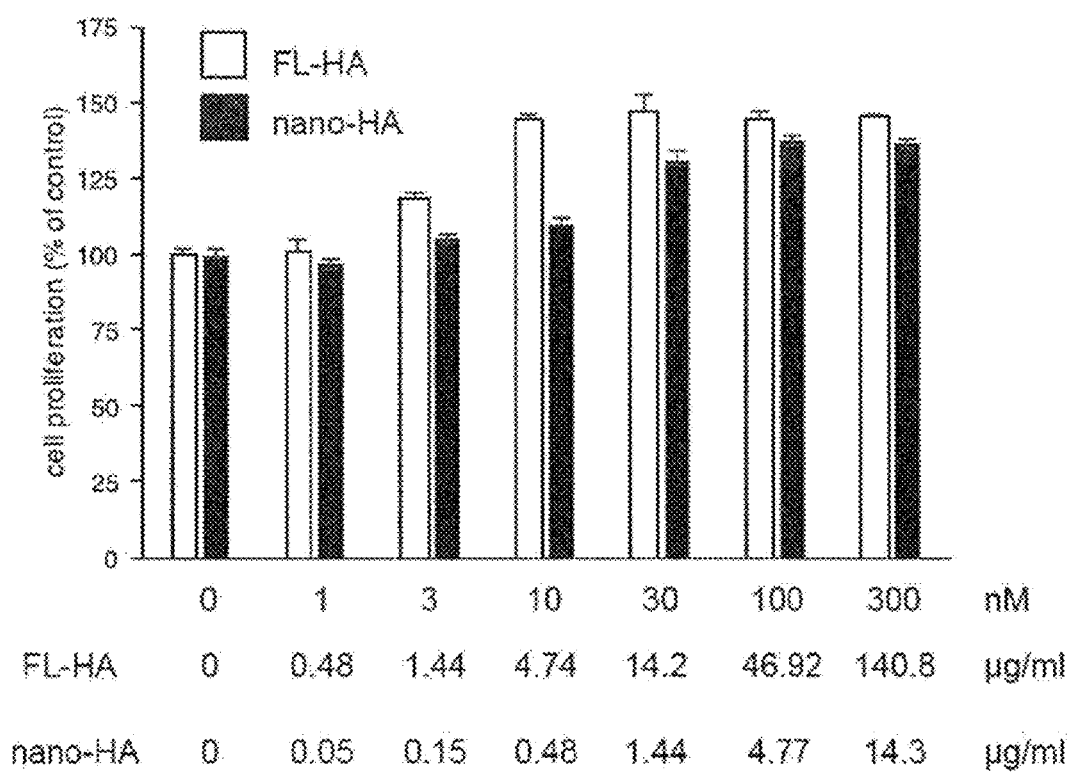
FIG. 17 is a drawing showing the effects of various concentrations of an FL-HA complex (FL-HA) of type B and a linked-mini (2+3)/CB-LD/YFDY complex (nano-HA) on the proliferation of MDCK cells. The number on the horizontal axis shows, from the top, molar concentrations (nM) of both HA complexes, a weight/volume concentration (μg/ml) of the FL-HA complex of type B, and a weight/volume concentration (μg/ml) of the linked-mini (2+3)/CB-LD/YFDY complex.
Figure 18:
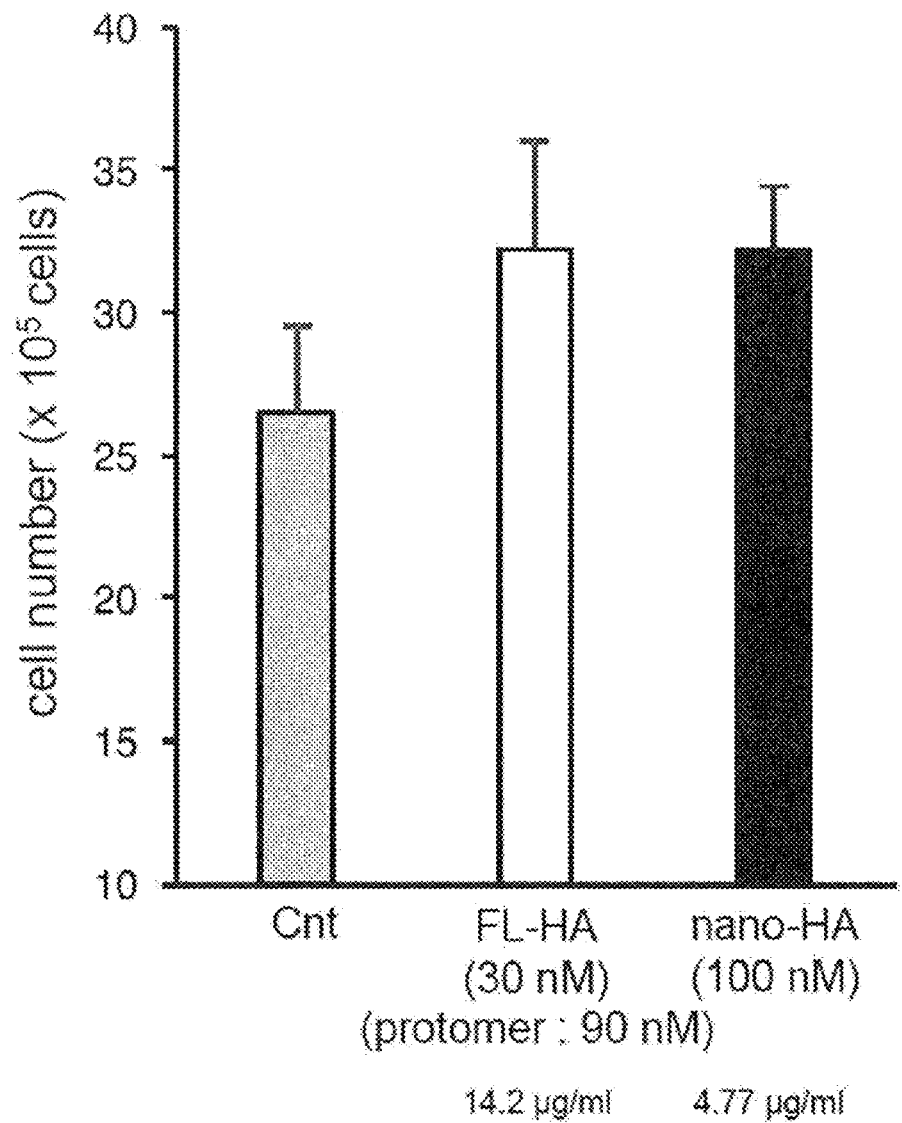
FIG. 18 is a drawing showing the effects of an FL-HA complex of type B (FL-HA; 30 nM (90 nM per single arm (protomer)) and a linked-mini (2+3)/CB-LD/YFDY complex (nano-HA; 100 nM) on the proliferation of MDCK cells. The numerical value in the lower panel of the horizontal axis shows a weight/volume concentration (μg/ml) of each HA complex.

When HA1, HA2 and HA3 subcomponents of type B were separately expressed, purified using a tag, mixed, incubated and reconstituted. By calculation with a constitution yield of 50-80% and conversion to culture of the total 3 L, 0.13-0.2 µmol was obtained with 3× protomer as 1 molecule, and 0.4-0.6 µmol as protomer. When HA2 and HA3 were linked via a linker, by conversion to culture of 3 L, 5.1 µmol of HA complex was obtained with linked-mini(2+3)/BB, 3.3 µmol of HA complex was obtained with linked-mini(2+3)/CB, and 8.4 µmol of HA complex was obtained with mutation-introduced linked-mini(2+3)/CB-YFDY, which was about 10 times higher yield per monovalent molecule.
(8) The mini-HA was added to the medium of MDCK cultured cells at a concentration of 100 nM and incubated. As a result, cell clumps in which some tens of cells were adhered were observed in the absence of mini-HA, whereas the cells were separated in the presence of mini-HA (FIG. 9).
(9) Various HA complex proteins were added at a concentration of 300 nM as a protomer to the medium of Caco-2 cells, and cytotoxicity was examined. No cytotoxicity was observed in any of the HA complexes except that the cell viability decreased in C-type FL-HA, and rather, a tendency to support cell survival was found (FIG. 10).
(10) Human iPS cell D2 strain was cultured for 3 days, linked-mini(2+3)/CB-LD/YFDY or FL-HA of type B was added to the medium for 24 hr from day 1 (Day1) to day 2 (Day2) from the start of culture, and changes in the cell form during culture were comparison observed. As a result, as shown in FIG. 16B, it was clarified that the addition of linked-mini(2+3)/CB-LD/YFDY inhibits cell-cell adhesion of iPS cell clump as with FL-HA. The linked-mini(2+3)/CB-LD/YFDY showed the cell-cell adhesion inhibitory effect at a concentration of not less than 50 nM (FIG. 16B shows only the results at 0.5-100 nM; however, the cell-cell adhesion inhibitory effect was shown without cytotoxicity even at higher concentrations (up to 450 nM)).
(11) By an SF assay, the MDCK cell proliferation promoting action of various concentrations (1-300 nM) of FL-HA and linked-mini(2+3)/CB-LD/YFDY was analyzed. As a result, the linked-mini(2+3)/CB-LD/YFDY showed a remarkable cell proliferation promoting action at not less than 30 nM, and showed about ⅓ of the effect as compared to the same molar concentration of FL-HA (single-arm: equivalent per protomer) (FIG. 17). Since the molecular weight of the linked-mini(2+3)/CB-LD/YFDY was about ⅒ that of FL-HA, when converted to a weight/volume concentration, the linked-mini(2+3)/CB-LD/YFDY showed about 3 times stronger activity as compared to FL-HA (FIG. 17).
(12) The proliferation promoting effect of HA in MDCK cells was analyzed by counting the number of the cells. As a result, the linked-mini(2+3)/CB-LD/YFDY showed a proliferation-promoting effect comparable to FL-HA at an equivalent molar concentration per single-arm (protomer) (FIG. 18). When converted to a weight/volume concentration, it showed about 3 times stronger activity as compared to FL-HA.

INDUSTRIAL APPLICABILITY

The HA complex protein of the present invention is miniaturized while maintaining the cadherin function inhibitory activity. Thus, the HA complex protein is advantageous over conventional products because it simplifies the production step and is easy to handle. In addition, it is low toxic and has a cell proliferation promoting action. Therefore, it is extremely useful as, for example, a medium additive for maintaining an undifferentiated state of pluripotent stem cells 3 including iPS cells and promoting cell proliferation.

This application is based on a patent application No. 2017-226370 filed in Japan (filing date: Nov. 24, 2017), the contents of which are incorporated in full herein.

```

The invention claimed is:

1. A miniaturized hemagglutinin complex protein having function inhibitory activity against E-cadherin, wherein the miniaturized hemagglutinin complex protein is selected from the group consisting of:
   (1) mini-HA consisting of HA1 subcomponent of SEQ ID NO:10, HA2 subcomponent of SEQ ID NO: 4, and HA3 subcomponent fragment of SEQ ID NO:2,
   (2) FL (2+3)-C consisting of HA2 subcomponent of SEQ ID NO:4 and HA3 component with Strep-Tag (C-terminus) of SEQ ID NO:44,
   (3) linked-mini (2+3)/BB of SEQ ID NO:47,
   (4) linked-mini (2+3)/CB of SEQ ID NO:48,
   (5) linked-mini (2+3)/CB-YFDY of SEQ ID NO:49, and
   (6) linked-mini (2+3)/CB-LD/YFDY of SEQ ID NO:50.

2. An E-cadherin function inhibitor comprising the hemagglutinin complex protein according to claim 1.

3. The inhibitor according to claim 2, wherein the function of E-cadherin is a cell-cell adhesion function.

4. A method for inhibiting cell-cell adhesion in a cell population comprising bringing the hemagglutinin complex protein according to claim 1 into contact with the cell population.

5. The method according to claim 4, wherein the cell population is a population of pluripotent stem cells.

6. A cell proliferation promoter comprising the hemagglutinin complex protein according to claim 1.

7. A method for promoting proliferation of a cell comprising culturing the cell in the presence of the hemagglutinin complex protein according to claim 1.

8. The miniaturized hemagglutinin complex protein according to claim 1, wherein the miniaturized hemagglutinin complex protein is selected from the group consisting of:
   (1) linked-mini (2+3)/BB of SEQ ID NO:47,
   (2) linked-mini (2+3)/CB of SEQ ID NO:48,
   (3) linked-mini (2+3)/CB-YFDY of SEQ ID NO:49, and
   (4) linked-mini (2+3)/CB-LD/YFDY of SEQ ID NO:50.

* * * * *

                        SEQUENCE LISTING

<160> NUMBER OF SEQ ID NOS: 52

<210> SEQ ID NO 1
<211> LENGTH: 247
<212> TYPE: PRT
<213> ORGANISM: Clostridium botulinum type A

<400> SEQUENCE: 1

Glu Asn Ile Gln Glu Ile Asn Thr Ala Ile Ser Asp Asn Tyr Thr Tyr
1               5                   10                  15

Asn Ile Pro Gly Ile Val Asn Asn Pro Phe Tyr Ile Leu Phe Thr
            20                  25                  30

Val Asn Thr Thr Gly Ile Tyr Lys Ile Asn Ala Gln Asn Asn Leu Pro
            35                  40                  45

Ser Leu Lys Ile Tyr Glu Ala Ile Gly Ser Gly Asn Arg Asn Phe Gln
    50                  55                  60

Ser Gly Asn Leu Cys Asp Asp Ile Lys Ala Ile Asn Tyr Ile Thr
65                  70                  75                  80

Gly Phe Asp Ser Pro Asn Ala Lys Ser Tyr Leu Val Val Leu Leu Asn
                85                  90                  95

Lys Asp Lys Asn Tyr Tyr Ile Arg Val Pro Gln Thr Ser Ser Asn Ile
                100                 105                 110

Glu Asn Gln Ile Gln Phe Lys Arg Glu Glu Gly Asp Leu Arg Asn Leu
            115                 120                 125

Met Asn Ser Ser Val Asn Ile Ile Asp Asn Leu Asn Ser Thr Gly Ala
    130                 135                 140

His Tyr Tyr Thr Arg Gln Ser Pro Asp Val His Asp Tyr Ile Ser Tyr
145                 150                 155                 160

Glu Phe Thr Ile Pro Gly Asn Phe Asn Asn Lys Asp Thr Ser Asn Ile
                165                 170                 175

Arg Leu Tyr Thr Ser Tyr Asn Gln Gly Ile Gly Thr Leu Phe Arg Val
                180                 185                 190

Thr Glu Thr Ile Asp Gly Tyr Asn Leu Ile Asn Ile Gln Gln Asn Leu
            195                 200                 205

His Leu Leu Asn Asn Thr Asn Ser Ile Arg Leu Leu Asn Gly Ala Ile
    210                 215                 220

Tyr Ile Leu Lys Val Glu Val Thr Glu Leu Asn Asn Tyr Asn Ile Arg
225                 230                 235                 240

Leu His Ile Asp Ile Thr Asn
                245

<210> SEQ ID NO 2
<211> LENGTH: 247
<212> TYPE: PRT
<213> ORGANISM: Clostridium botulinum type B

<400> SEQUENCE: 2

Glu Asn Ile Gln Glu Ile Asn Thr Ala Ile Ser Asp Asn Tyr Thr Tyr
1               5                   10                  15

Asn Ile Pro Gly Ile Val Asn Asn Pro Phe Tyr Ile Leu Phe Thr
            20                  25                  30

Val Asn Thr Thr Gly Ile Tyr Lys Ile Asn Ala Gln Asn Asn Leu Pro
            35                  40                  45
```

```
Ser Leu Lys Ile Tyr Glu Ala Ile Gly Ser Gly Asn Arg Asn Phe Gln
    50                  55                  60

Ser Gly Asn Leu Cys Asp Asp Ile Lys Ala Ile Asn Tyr Ile Thr
65                  70                  75                  80

Gly Phe Asp Ser Pro Asn Ala Lys Ser Tyr Leu Val Val Leu Leu Asn
                    85                  90                  95

Lys Asp Lys Asn Tyr Tyr Ile Arg Val Pro Gln Thr Ser Ser Asn Ile
                100                 105                 110

Glu Asn Gln Ile Lys Phe Lys Arg Glu Gly Asp Leu Arg Asn Leu
            115                 120                 125

Met Asn Ser Ser Val Asn Ile Ile Asp Asn Leu Asn Ser Thr Gly Ala
    130                 135                 140

His Tyr Tyr Thr Arg Gln Ser Pro Asp Val His Asp Tyr Ile Ser Tyr
145                 150                 155                 160

Glu Phe Thr Ile Pro Gly Asn Phe Asn Asn Lys Asp Thr Ser Asn Ile
                165                 170                 175

Arg Leu Tyr Thr Ser Tyr Asn Gln Gly Ile Gly Thr Leu Phe Arg Val
                180                 185                 190

Thr Glu Thr Ile Asp Gly Tyr Asn Leu Ile Asn Ile Gln Gln Asn Leu
                195                 200                 205

Asn Leu Leu Asn Ser Thr Lys Ser Ile Arg Leu Leu Asn Gly Ala Ile
        210                 215                 220

Tyr Ile Leu Lys Val Glu Val Thr Glu Leu Asn Asn Tyr Asn Ile Lys
225                 230                 235                 240

Leu His Ile Asp Ile Thr Asn
                245

<210> SEQ ID NO 3
<211> LENGTH: 146
<212> TYPE: PRT
<213> ORGANISM: Clostridium botulinum type A

<400> SEQUENCE: 3

Met Ser Val Glu Arg Thr Phe Leu Pro Asn Gly Asn Tyr Asn Ile Lys
1               5                   10                  15

Ser Ile Phe Ser Gly Ser Leu Tyr Leu Asn Pro Val Ser Lys Ser Leu
                20                  25                  30

Thr Phe Ser Asn Glu Ser Ser Ala Asn Asn Gln Lys Trp Asn Val Glu
            35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Tyr Ala Trp
            100                 105                 110

Asp Ile Tyr Asp Thr Asn Glu Asn Ile Leu Ser Gln Pro Leu Leu Leu
        115                 120                 125

Leu Pro Asn Phe Asp Ile Tyr Asn Ser Asn Gln Met Phe Lys Leu Glu
    130                 135                 140

Lys Ile
145
```

<210> SEQ ID NO 4
<211> LENGTH: 146
<212> TYPE: PRT
<213> ORGANISM: Clostridium botulinum type B

<400> SEQUENCE: 4

Met Ser Ala Glu Arg Thr Phe Leu Pro Asn Gly Asn Tyr Asn Ile Lys
1               5                   10                  15

Ser Ile Phe Ser Gly Ser Leu Tyr Leu Ser Pro Val Ser Gly Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
        115                 120                 125

Leu Pro Asn Phe Asp Ile Tyr Asn Ser Asn Gln Met Phe Lys Leu Glu
    130                 135                 140

Lys Ile
145

<210> SEQ ID NO 5
<211> LENGTH: 146
<212> TYPE: PRT
<213> ORGANISM: Clostridium botulinum type C

<400> SEQUENCE: 5

Met Ser Ser Glu Arg Thr Phe Leu Pro Asn Gly Asn Tyr Lys Ile Lys
1               5                   10                  15

Ser Leu Phe Ser Asp Ser Leu Tyr Leu Thr Tyr Ser Ser Gly Ala Leu
            20                  25                  30

Ser Phe Ser Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
    50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Ile Thr Asp Gln Pro Ile Leu Asn
        115                 120                 125

Leu Pro Asn Phe Asp Ile Asn Asn Ser Asn Gln Ile Leu Lys Leu Glu
    130                 135                 140

Lys Leu
145

<210> SEQ ID NO 6
<211> LENGTH: 146
<212> TYPE: PRT

<213> ORGANISM: Clostridium phage D-1873

<400> SEQUENCE: 6

| | | | | | | | | | | | | | | |
|---|---|---|---|---|---|---|---|---|---|---|---|---|---|---|
|Met|Ser|Ser|Glu|Arg|Thr|Phe|Leu|Pro|Asn|Gly|Asn|Tyr|Lys|Ile|Lys|
|1| | | |5| | | |10| | | |15| | |

Ser Leu Phe Ser Asn Ser Leu Tyr Leu Thr Tyr Ser Ser Gly Ala Leu
            20                  25                  30

Ser Phe Ser Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
    50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Ile Thr Asp Gln Pro Ile Leu Asn
        115                 120                 125

Leu Pro Asn Phe Asp Ile Asn Asn Ser Asn Gln Ile Leu Lys Leu Glu
    130                 135                 140

Lys Leu
145

<210> SEQ ID NO 7
<211> LENGTH: 626
<212> TYPE: PRT
<213> ORGANISM: Clostridium botulinum type A

<400> SEQUENCE: 7

Met Asn Ser Ser Ile Lys Lys Ile Tyr Asn Asp Ile Gln Glu Lys Val
1               5                   10                  15

Ile Asn Tyr Ser Asp Thr Ile Asp Leu Ala Asp Gly Asn Tyr Val Val
            20                  25                  30

Arg Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
    50                  55                  60

Val Asn Asp Asn Ala Ile Pro Tyr Tyr Tyr Pro Thr Pro Ser Phe Asn
65                  70                  75                  80

Glu Glu Tyr Ile Lys Asn Asn Ile Gln Thr Val Phe Thr Asn Phe Thr
                85                  90                  95

Glu Ala Asn Gln Ile Pro Ile Gly Phe Glu Phe Ser Lys Thr Ala Pro
            100                 105                 110

Ser Asn Lys Asn Leu Tyr Met Tyr Leu Gln Tyr Thr Tyr Ile Arg Tyr
        115                 120                 125

Glu Ile Ile Lys Val Leu Gln His Glu Ile Glu Arg Ala Val Leu
    130                 135                 140

Tyr Val Pro Ser Leu Gly Tyr Val Lys Ser Ile Glu Phe Asn Pro Gly
145                 150                 155                 160

Glu Lys Ile Asn Lys Asp Phe Tyr Phe Leu Thr Asn Asp Lys Cys Ile
                165                 170                 175

Leu Asn Glu Gln Phe Leu Tyr Lys Lys Ile Leu Glu Thr Thr Lys Asn
            180                 185                 190

Ile Pro Thr Asn Asn Ile Phe Asn Ser Lys Val Ser Ser Thr Gln Arg

-continued

```
            195                 200                 205
Val Leu Pro Tyr Ser Asn Gly Leu Tyr Val Ile Asn Lys Gly Asp Gly
210                 215                 220

Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                    245                 250                 255

Arg Pro Leu Phe Thr Thr Ser Asn Asp Thr Lys Phe Ser Gln Gln Tyr
                260                 265                 270

Thr Glu Glu Arg Leu Lys Asp Ala Phe Asn Val Gln Leu Phe Asn Thr
            275                 280                 285

Ser Thr Ser Leu Phe Lys Phe Val Glu Glu Ala Pro Ser Asp Lys Asn
        290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                    325                 330                 335

Leu Gly Tyr Cys Glu Val Thr Asn Ala Pro Ser Pro Glu Ser Glu Val
                340                 345                 350

Val Lys Met Gln Val Ala Glu Asp Gly Phe Ile Gln Asn Gly Pro Glu
            355                 360                 365

Glu Glu Ile Val Val Gly Val Ile Asp Pro Ser Glu Asn Ile Gln Glu
        370                 375                 380

Ile Asn Thr Ala Ile Ser Asp Asn Tyr Thr Tyr Asn Ile Pro Gly Ile
385                 390                 395                 400

Val Asn Asn Asn Pro Phe Tyr Ile Leu Phe Thr Val Asn Thr Thr Gly
                    405                 410                 415

Ile Tyr Lys Ile Asn Ala Gln Asn Asn Leu Pro Ser Leu Lys Ile Tyr
                420                 425                 430

Glu Ala Ile Gly Ser Gly Asn Arg Asn Phe Gln Ser Gly Asn Leu Cys
            435                 440                 445

Asp Asp Asp Ile Lys Ala Ile Asn Tyr Ile Thr Gly Phe Asp Ser Pro
        450                 455                 460

Asn Ala Lys Ser Tyr Leu Val Val Leu Leu Asn Lys Asp Lys Asn Tyr
465                 470                 475                 480

Tyr Ile Arg Val Pro Gln Thr Ser Ser Asn Ile Glu Asn Gln Ile Gln
                    485                 490                 495

Phe Lys Arg Glu Glu Gly Asp Leu Arg Asn Leu Met Asn Ser Ser Val
                500                 505                 510

Asn Ile Ile Asp Asn Leu Asn Ser Thr Gly Ala His Tyr Tyr Thr Arg
            515                 520                 525

Gln Ser Pro Asp Val His Asp Tyr Ile Ser Tyr Glu Phe Thr Ile Pro
        530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                    565                 570                 575

Gly Tyr Asn Leu Ile Asn Ile Gln Gln Asn Leu His Leu Leu Asn Asn
                580                 585                 590

Thr Asn Ser Ile Arg Leu Leu Asn Gly Ala Ile Tyr Ile Leu Lys Val
            595                 600                 605

Glu Val Thr Glu Leu Asn Asn Tyr Asn Ile Arg Leu His Ile Asp Ile
        610                 615                 620
```

Thr Asn
625

<210> SEQ ID NO 8
<211> LENGTH: 626
<212> TYPE: PRT
<213> ORGANISM: Clostridium botulinum type B

<400> SEQUENCE: 8

Met Asn Ser Ser Ile Lys Lys Ile Tyr Asn His Ile Gln Glu Lys Val
1               5                   10                  15

Ile Asn Tyr Ser Asp Thr Ile Asp Leu Ala Asp Gly Asn Tyr Val Val
            20                  25                  30

Ser Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
    50                  55                  60

Val Asn Asp Asn Ala Ile Pro Tyr Tyr Pro Thr Pro Ser Phe Asn
65                  70                  75                  80

Glu Glu Tyr Ile Lys Asn Asn Ile Gln Thr Val Phe Ala Asn Phe Thr
                85                  90                  95

Glu Ala Asn Gln Ile Pro Ile Gly Phe Glu Phe Ser Lys Thr Ala Pro
            100                 105                 110

Ser Asn Lys Asn Leu Tyr Met Tyr Leu Gln Tyr Thr Tyr Ile Arg Tyr
        115                 120                 125

Glu Ile Ile Lys Val Leu Gln His Glu Ile Ile Glu Arg Ala Val Leu
    130                 135                 140

Tyr Val Pro Ser Leu Gly Tyr Val Lys Ser Ile Glu Phe Asn Pro Gly
145                 150                 155                 160

Glu Lys Ile Asn Lys Asp Phe Tyr Phe Leu Thr Asn Asp Lys Cys Ile
                165                 170                 175

Leu Asn Glu Gln Phe Leu Tyr Lys Lys Ile Leu Glu Thr Thr Lys Asn
            180                 185                 190

Ile Pro Thr Asn Asn Ile Phe Asn Ser Lys Val Ser Ser Thr Gln Arg
        195                 200                 205

Val Leu Pro Tyr Ser Asn Gly Leu Tyr Val Ile Asn Lys Gly Asp Gly
    210                 215                 220

Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Ala Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asn Lys Asn
    290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val
            340                 345                 350

Val Lys Thr Gln Val Ala Glu Asp Gly Phe Ile Gln Asn Gly Pro Glu

-continued

```
                355                 360                 365
Glu Glu Ile Val Val Gly Val Ile Asp Pro Ser Glu Asn Ile Gln Glu
        370                 375                 380
Ile Asn Thr Ala Ile Ser Asp Asn Tyr Thr Tyr Asn Ile Pro Gly Ile
385                 390                 395                 400
Val Asn Asn Asn Pro Phe Tyr Ile Leu Phe Thr Val Asn Thr Thr Gly
                405                 410                 415
Ile Tyr Lys Ile Asn Ala Gln Asn Asn Leu Pro Ser Leu Lys Ile Tyr
            420                 425                 430
Glu Ala Ile Gly Ser Gly Asn Arg Asn Phe Gln Ser Gly Asn Leu Cys
                435                 440                 445
Asp Asp Asp Ile Lys Ala Ile Asn Tyr Ile Thr Gly Phe Asp Ser Pro
        450                 455                 460
Asn Ala Lys Ser Tyr Leu Val Val Leu Asn Lys Asp Lys Asn Tyr
465                 470                 475                 480
Tyr Ile Arg Val Pro Gln Thr Ser Ser Asn Ile Glu Asn Gln Ile Lys
                485                 490                 495
Phe Lys Arg Glu Glu Gly Asp Leu Arg Asn Leu Met Asn Ser Ser Val
            500                 505                 510
Asn Ile Ile Asp Asn Leu Asn Ser Thr Gly Ala His Tyr Tyr Thr Arg
                515                 520                 525
Gln Ser Pro Asp Val His Asp Tyr Ile Ser Tyr Glu Phe Thr Ile Pro
        530                 535                 540
Gly Asn Phe Asn Asn Lys Asp Thr Ser Asn Ile Arg Leu Tyr Thr Ser
545                 550                 555                 560
Tyr Asn Gln Gly Ile Gly Thr Leu Phe Arg Val Thr Glu Thr Ile Asp
                565                 570                 575
Gly Tyr Asn Leu Ile Asn Ile Gln Gln Asn Leu Asn Leu Leu Asn Ser
            580                 585                 590
Thr Lys Ser Ile Arg Leu Leu Asn Gly Ala Ile Tyr Ile Leu Lys Val
                595                 600                 605
Glu Val Thr Glu Leu Asn Asn Tyr Asn Ile Lys Leu His Ile Asp Ile
        610                 615                 620
Thr Asn
625

<210> SEQ ID NO 9
<211> LENGTH: 293
<212> TYPE: PRT
<213> ORGANISM: Clostridium botulinum type A

<400> SEQUENCE: 9

Met Glu His Tyr Ser Val Ile Gln Asn Ser Leu Asn Asp Lys Ile Val
1               5                   10                  15
Thr Ile Ser Cys Lys Ala Asp Thr Asn Leu Phe Phe Tyr Gln Val Ala
                20                  25                  30
Gly Asn Val Ser Leu Phe Gln Gln Thr Arg Asn Tyr Leu Glu Arg Trp
            35                  40                  45
Arg Leu Ile Tyr Asp Ser Asn Lys Ala Ala Tyr Lys Ile Lys Ser Met
    50                  55                  60
Asp Ile His Asn Thr Asn Leu Val Leu Thr Trp Asn Ala Pro Thr His
65                  70                  75                  80
Asn Ile Ser Thr Gln Gln Asp Ser Asn Ala Asp Asn Gln Tyr Trp Leu
                85                  90                  95
```

```
Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
            115                 120                 125

Leu Ser Thr Leu Asn Asn Ser Asn Tyr Ile Lys Phe Ile Ile Glu Asp
        130                 135                 140

Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
            195                 200                 205

Ser Asn Gly Val Leu Thr Trp Ile Phe Ser Asn Gly Asn Thr Val Arg
        210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Gly Gly Gln Thr Ala Asn Gly
            260                 265                 270

Thr Ala Ile Gln Val Phe Asn Tyr His Gly Asp Asp Asn Gln Lys Trp
        275                 280                 285

Asn Ile Arg Asn Pro
    290

<210> SEQ ID NO 10
<211> LENGTH: 294
<212> TYPE: PRT
<213> ORGANISM: Clostridium botulinum type B

<400> SEQUENCE: 10

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
    50                  55                  60

Ser Met Asn Ile Tyr Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
    130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175
```

```
Leu Ala Val Asn Leu Tyr Ile Trp Asn Asn Asp Leu Asn Gln Lys Trp
            180                 185                 190

Thr Ile Ile Tyr Asn Glu Glu Lys Ala Ala Tyr Gln Phe Phe Asn Lys
            195                 200                 205

Ile Leu Ser Asn Gly Val Leu Thr Trp Ile Phe Ser Asp Gly Asn Thr
            210                 215                 220

Val Arg Val Ser Ser Ala Gln Asn Asp Ala Gln Tyr Trp Leu
225                 230                 235                 240

Ile Asn Pro Val Ser Asp Asn Tyr Asp Arg Tyr Thr Ile Thr Asn Leu
                245                 250                 255

Arg Asp Lys Thr Lys Val Leu Asp Leu Tyr Gly Gly Gln Thr Ala Asp
                260                 265                 270

Gly Thr Thr Ile Gln Val Phe Asn Ser Asn Gly Gly Asp Asn Gln Ile
            275                 280                 285

Trp Thr Met Ser Asn Pro
    290

<210> SEQ ID NO 11
<211> LENGTH: 286
<212> TYPE: PRT
<213> ORGANISM: Clostridium botulinum type C

<400> SEQUENCE: 11

Met Ser Gln Thr Asn Ala Asn Asp Leu Arg Asn Asn Glu Val Phe Phe
1               5                   10                  15

Ile Ser Pro Ser Asn Asn Thr Asn Lys Val Leu Asp Lys Ile Ser Gln
            20                  25                  30

Ser Glu Val Lys Leu Trp Asn Lys Leu Ser Gly Ala Asn Gln Lys Trp
            35                  40                  45

Arg Leu Ile Tyr Asp Thr Asn Lys Gln Ala Tyr Lys Ile Lys Val Met
    50                  55                  60

Asp Asn Thr Ser Leu Ile Leu Thr Trp Asn Ala Pro Leu Ser Ser Val
65                  70                  75                  80

Ser Val Lys Thr Asp Thr Asn Gly Asp Asn Gln Tyr Trp Tyr Leu Leu
                85                  90                  95

Gln Asn Tyr Ile Ser Arg Asn Val Ile Ile Arg Asn Tyr Met Asn Pro
            100                 105                 110

Asn Leu Val Leu Gln Tyr Asn Ile Asp Asp Thr Leu Met Val Ser Thr
            115                 120                 125

Gln Thr Ser Ser Asn Gln Phe Phe Lys Phe Ser Asn Cys Ile Tyr
    130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Gln Lys Trp Ile Ile Glu Tyr Asn Glu
            180                 185                 190

Thr Lys Ser Ala Tyr Thr Leu Lys Cys Gln Glu Asn Asn Arg Tyr Leu
            195                 200                 205

Thr Trp Ile Gln Asn Ser Asn Tyr Val Glu Thr Tyr Gln Ser Thr
    210                 215                 220

Asp Ser Leu Ile Gln Tyr Trp Asn Ile Asn Tyr Leu Asp Asn Asp Ala
225                 230                 235                 240

Ser Lys Tyr Ile Leu Tyr Asn Leu Gln Asp Thr Asn Arg Val Leu Asp
```

```
                        245                 250                 255
Val Tyr Asn Ser Gln Ile Ala Asn Gly Thr His Val Ile Val Asp Ser
                260                 265                 270
Tyr His Gly Asn Thr Asn Gln Gln Trp Ile Ile Asn Leu Ile
            275                 280                 285

<210> SEQ ID NO 12
<211> LENGTH: 285
<212> TYPE: PRT
<213> ORGANISM: Clostridium phage D-1873

<400> SEQUENCE: 12

Met Ser Gln Thr Asn Ala Asn Asp Leu Arg Asn Asn Glu Val Phe Phe
1               5                   10                  15
Ile Ser Pro Ser Asn Asn Thr Asn Lys Val Leu Asp Lys Ile Ser Gln
            20                  25                  30
Ser Glu Val Lys Leu Trp Asn Lys Leu Ser Gly Ala Asn Gln Lys Trp
        35                  40                  45
Arg Leu Ile Tyr Asp Thr Asn Lys Gln Ala Tyr Lys Ile Lys Val Met
    50                  55                  60
Asp Asn Thr Ser Leu Ile Leu Thr Trp Asn Ala Pro Leu Ser Ser Val
65                  70                  75                  80
Ser Val Lys Thr Asp Thr Asn Gly Asp Asn Gln Tyr Trp Tyr Leu Leu
                85                  90                  95
Gln Asn Tyr Ile Ser Arg Asn Val Ile Ile Arg Asn Tyr Met Asn Pro
            100                 105                 110
Asn Leu Val Leu Gln Tyr Asn Ile Asp Asp Thr Leu Met Val Ser Thr
        115                 120                 125
Gln Thr Ser Ser Asn Gln Phe Phe Lys Phe Ser Asn Cys Ile Tyr
    130                 135                 140
Glu Ser Phe Asn Asn Ser Thr Cys Lys Ile Gln Thr Ser Leu Thr Ile
145                 150                 155                 160
Lys Phe Ile Asp Lys Asn Gln Asn Ser Asn Asn Val Thr Ile Trp Ser
                165                 170                 175
Trp Asn Asn Gly Asp Asn Gln Lys Trp Lys Ile Leu Tyr Asn Glu Ser
            180                 185                 190
Lys Met Ala Tyr Thr Leu Thr Cys Ile Lys Asn Asn Glu Tyr Leu Thr
        195                 200                 205
Trp Phe Ser Ser Ile Gly Asn Asn Val Gly Thr Tyr Arg Thr Glu Gly
    210                 215                 220
Asn Asn Asp Gln Tyr Trp Phe Ile Asn Tyr Leu Asn Asn Asp Ala Ser
225                 230                 235                 240
Met Tyr Thr Ile Ser Asn Phe Ser Asn Gln Ser Lys Phe Leu Asp Val
                245                 250                 255
Val Asn Ser Gly Leu Ala Asp Gly Thr Asn Val Gln Val Trp Asp Ser
            260                 265                 270
Asn Gly Thr Ser Ala Gln Lys Trp Ile Ile Thr Arg Leu
        275                 280                 285

<210> SEQ ID NO 13
<211> LENGTH: 9
<212> TYPE: PRT
<213> ORGANISM: Artificial Sequence
<220> FEATURE:
<223> OTHER INFORMATION: Synthetic sequence, linker peptide

<400> SEQUENCE: 13
```

Gly Ser Gly Gly Asp Asp Pro Pro Gly
1               5

<210> SEQ ID NO 14
<211> LENGTH: 72
<212> TYPE: DNA
<213> ORGANISM: Artificial Sequence
<220> FEATURE:
<223> OTHER INFORMATION: Synthetic sequence, primer

<400> SEQUENCE: 14
taccatggct agcgcaagct acggatccgg tagtgcatgg agccaccgc agttcgaaaa    60 gtaagtcgac gc                                                       72

<210> SEQ ID NO 15
<211> LENGTH: 72
<212> TYPE: DNA
<213> ORGANISM: Artificial Sequence
<220> FEATURE:
<223> OTHER INFORMATION: Synthetic sequence, primer

<400> SEQUENCE: 15
gcgtcgactt actttttcgaa ctgcgggtgg ctccatgcac taccggatcc gtagcttgcg    60
ctagccatgg ta                                                        72

<210> SEQ ID NO 16
<211> LENGTH: 30
<212> TYPE: DNA
<213> ORGANISM: Artificial Sequence
<220> FEATURE:
<223> OTHER INFORMATION: Synthetic sequence, primer

<400> SEQUENCE: 16
ctagctagca tccaaaattc attaaatgac                                      30

<210> SEQ ID NO 17
<211> LENGTH: 57
<212> TYPE: DNA
<213> ORGANISM: Artificial Sequence
<220> FEATURE:
<223> OTHER INFORMATION: Synthetic sequence, primer

<400> SEQUENCE: 17
cgggatcctt acttgtcgtc atcgtctttg tagtctgggt tactcatagt ccatatc       57

<210> SEQ ID NO 18
<211> LENGTH: 31
<212> TYPE: DNA
<213> ORGANISM: Artificial Sequence
<220> FEATURE:
<223> OTHER INFORMATION: Synthetic sequence, primer

<400> SEQUENCE: 18
ctagctagct cagctgaaag aactttttcta c                                    31

<210> SEQ ID NO 19
<211> LENGTH: 36
<212> TYPE: DNA
<213> ORGANISM: Artificial Sequence
<220> FEATURE:
<223> OTHER INFORMATION: Synthetic sequence, primer

<400> SEQUENCE: 19
ccgctcgagt tatattttttt caagtttgaa catttg                              36

<210> SEQ ID NO 20
<211> LENGTH: 31
<212> TYPE: DNA
<213> ORGANISM: Artificial Sequence
<220> FEATURE:
<223> OTHER INFORMATION: Synthetic sequence, primer

<400> SEQUENCE: 20
gaaaaagggt accaatatag tgatactatt g                           31

<210> SEQ ID NO 21
<211> LENGTH: 31
<212> TYPE: DNA
<213> ORGANISM: Artificial Sequence
<220> FEATURE:
<223> OTHER INFORMATION: Synthetic sequence, primer

<400> SEQUENCE: 21
cgtgtcgact taattagtaa tatctatatg c                           31

<210> SEQ ID NO 22
<211> LENGTH: 39
<212> TYPE: DNA
<213> ORGANISM: Artificial Sequence
<220> FEATURE:
<223> OTHER INFORMATION: Synthetic sequence, primer

<400> SEQUENCE: 22
gcgctagcaa tatagtgata ctattgattt agctgatgg                   39

<210> SEQ ID NO 23
<211> LENGTH: 42
<212> TYPE: DNA
<213> ORGANISM: Artificial Sequence
<220> FEATURE:
<223> OTHER INFORMATION: Synthetic sequence, primer

<400> SEQUENCE: 23
ccggatccat tagtaatatc tatatgcaat tttatattat ag               42

<210> SEQ ID NO 24
<211> LENGTH: 48
<212> TYPE: DNA
<213> ORGANISM: Artificial Sequence
<220> FEATURE:
<223> OTHER INFORMATION: Synthetic sequence, primer

<400> SEQUENCE: 24
ggggtgatga ccctccagga tcagctgaaa gaactttct acctaatg          48

<210> SEQ ID NO 25
<211> LENGTH: 36
<212> TYPE: DNA
<213> ORGANISM: Artificial Sequence
<220> FEATURE:
<223> OTHER INFORMATION: Synthetic sequence, primer

<400> SEQUENCE: 25
actaccggat cctatttttt caagtttgaa catttg                      36

<210> SEQ ID NO 26
<211> LENGTH: 26
<212> TYPE: DNA
<213> ORGANISM: Artificial Sequence
<220> FEATURE:

<223> OTHER INFORMATION: Synthetic sequence, primer

<400> SEQUENCE: 26
taagaaggag ataccatg gctagc                                                    26

<210> SEQ ID NO 27
<211> LENGTH: 53
<212> TYPE: DNA
<213> ORGANISM: Artificial Sequence
<220> FEATURE:
<223> OTHER INFORMATION: Synthetic sequence, primer

<400> SEQUENCE: 27
gggtcatcac ccccacttcc attagtaata tctatatgca attttatatt ata                    53

<210> SEQ ID NO 28
<211> LENGTH: 42
<212> TYPE: DNA
<213> ORGANISM: Artificial Sequence
<220> FEATURE:
<223> OTHER INFORMATION: Synthetic sequence, primer

<400> SEQUENCE: 28
gcgctagcga aaatatacaa gaaataaata ctgctatttc ag                                42

<210> SEQ ID NO 29
<211> LENGTH: 31
<212> TYPE: DNA
<213> ORGANISM: Artificial Sequence
<220> FEATURE:
<223> OTHER INFORMATION: Synthetic sequence, primer

<400> SEQUENCE: 29
ctagctagct caagtgaaag aacctttta c                                             31

<210> SEQ ID NO 30
<211> LENGTH: 37
<212> TYPE: DNA
<213> ORGANISM: Artificial Sequence
<220> FEATURE:
<223> OTHER INFORMATION: Synthetic sequence, primer

<400> SEQUENCE: 30
acgcgtcgac ttaaagtttt tctaatttta aaatttg                                      37

<210> SEQ ID NO 31
<211> LENGTH: 48
<212> TYPE: DNA
<213> ORGANISM: Artificial Sequence
<220> FEATURE:
<223> OTHER INFORMATION: Synthetic sequence, primer

<400> SEQUENCE: 31
ggggtgatga ccctccagga tcaagtgaaa gaacctttt acctaatg                           48

<210> SEQ ID NO 32
<211> LENGTH: 41
<212> TYPE: DNA
<213> ORGANISM: Artificial Sequence
<220> FEATURE:
<223> OTHER INFORMATION: Synthetic sequence, primer

<400> SEQUENCE: 32
actaccggat ccaagttttt ctaattttaa aatttgatta g                                 41

```
<210> SEQ ID NO 33
<211> LENGTH: 43
<212> TYPE: DNA
<213> ORGANISM: Artificial Sequence
<220> FEATURE:
<223> OTHER INFORMATION: Synthetic sequence, primer

<400> SEQUENCE: 33
atgatgatgg ttatatctat ttaagttcat catctaataa tag            43

<210> SEQ ID NO 34
<211> LENGTH: 40
<212> TYPE: DNA
<213> ORGANISM: Artificial Sequence
<220> FEATURE:
<223> OTHER INFORMATION: Synthetic sequence, primer

<400> SEQUENCE: 34
agatataacc atcatcatta taagctaaat atttattagg                40

<210> SEQ ID NO 35
<211> LENGTH: 38
<212> TYPE: DNA
<213> ORGANISM: Artificial Sequence
<220> FEATURE:
<223> OTHER INFORMATION: Synthetic sequence, primer

<400> SEQUENCE: 35
aatccttgta aaattgctat aaattcttat attatatg                  38

<210> SEQ ID NO 36
<211> LENGTH: 32
<212> TYPE: DNA
<213> ORGANISM: Artificial Sequence
<220> FEATURE:
<223> OTHER INFORMATION: Synthetic sequence, primer

<400> SEQUENCE: 36
aattttacaa ggattccata aactattatt ag                        32

<210> SEQ ID NO 37
<211> LENGTH: 32
<212> TYPE: DNA
<213> ORGANISM: Artificial Sequence
<220> FEATURE:
<223> OTHER INFORMATION: Synthetic sequence, primer

<400> SEQUENCE: 37
agagtctgtg aaactattga cggctataat tt                        32

<210> SEQ ID NO 38
<211> LENGTH: 32
<212> TYPE: DNA
<213> ORGANISM: Artificial Sequence
<220> FEATURE:
<223> OTHER INFORMATION: Synthetic sequence, primer

<400> SEQUENCE: 38
agtttcacag actctaaata aagtacctat tc                        32

<210> SEQ ID NO 39
<211> LENGTH: 31
<212> TYPE: DNA
<213> ORGANISM: Artificial Sequence
<220> FEATURE:
<223> OTHER INFORMATION: Synthetic sequence, primer
```

```
<400> SEQUENCE: 39
tcttctgatg ataatcaaaa atggaagtta g                                    31

<210> SEQ ID NO 40
<211> LENGTH: 35
<212> TYPE: DNA
<213> ORGANISM: Artificial Sequence
<220> FEATURE:
<223> OTHER INFORMATION: Synthetic sequence, primer

<400> SEQUENCE: 40
attatcatca gaagatgtat ttgaaaatga taatg                                35

<210> SEQ ID NO 41
<211> LENGTH: 319
<212> TYPE: PRT
<213> ORGANISM: Artificial Sequence
<220> FEATURE:
<223> OTHER INFORMATION: Synthetic sequence, His-BHA1-Flag

<400> SEQUENCE: 41
```

Met Gly Ser Ser His His His His His His Ser Ser Gly Leu Val Pro
1               5                   10                  15

Arg Gly Ser His Met Ala Ser Ile Gln Asn Ser Leu Asn Asp Lys Ile
            20                  25                  30

Val Thr Ile Ser Cys Lys Ala Asn Thr Asp Leu Phe Phe Tyr Gln Val
        35                  40                  45

Pro Gly Asn Gly Asn Val Ser Leu Phe Gln Gln Thr Arg Asn Tyr Leu
    50                  55                  60

Glu Arg Trp Arg Ile Ile Tyr Asp Ser Asn Lys Ala Ala Tyr Lys Ile
65                  70                  75                  80

Lys Ser Met Asn Ile Tyr Asn Thr Asn Leu Val Leu Thr Trp Asn Ala
                85                  90                  95

Pro Thr His Asn Ile Ser Ala Gln Gln Asp Ser Asn Ala Asp Asn Gln
            100                 105                 110

Tyr Trp Leu Leu Leu Lys Asp Ile Gly Asn Asn Ser Phe Ile Ile Ala
        115                 120                 125

Ser Tyr Lys Asn Pro Asn Leu Val Leu Tyr Ala Asp Thr Val Ala Arg
    130                 135                 140

Asn Leu Lys Leu Ser Thr Leu Asn Asn Ser Ser Tyr Ile Lys Phe Ile
145                 150                 155                 160

Ile Glu Asp Tyr Val Ile Ser Asp Phe Lys Asn Phe Thr Cys Arg Ile
                165                 170                 175

Ser Pro Ile Leu Ala Gly Gly Lys Val Val Gln Gln Val Ser Met Thr
            180                 185                 190

Asn Leu Ala Val Asn Leu Tyr Ile Trp Asn Asn Asp Leu Asn Gln Lys
        195                 200                 205

Trp Thr Ile Ile Tyr Asn Glu Glu Lys Ala Ala Tyr Gln Phe Phe Asn
    210                 215                 220

Lys Ile Leu Ser Asn Gly Val Leu Thr Trp Ile Phe Ser Asp Gly Asn
225                 230                 235                 240

Thr Val Arg Val Ser Ser Ala Gln Asn Asn Asp Ala Gln Tyr Trp
                245                 250                 255

Leu Ile Asn Pro Val Ser Asp Asn Tyr Asp Arg Tyr Thr Ile Thr Asn
            260                 265                 270

Leu Arg Asp Lys Thr Lys Val Leu Asp Leu Tyr Gly Gly Gln Thr Ala
        275                 280                 285

Asp Gly Thr Thr Ile Gln Val Phe Asn Ser Asn Gly Gly Asp Asn Gln
            290                 295                 300

Ile Trp Thr Met Ser Asn Pro Asp Tyr Lys Asp Asp Asp Lys
305                 310                 315

<210> SEQ ID NO 42
<211> LENGTH: 168
<212> TYPE: PRT
<213> ORGANISM: Artificial Sequence
<220> FEATURE:
<223> OTHER INFORMATION: Synthetic sequence, His-BHA2

<400> SEQUENCE: 42

Met Gly Ser Ser His His His His His His Ser Ser Gly Leu Val Pro
1               5                   10                  15

Arg Gly Ser His Met Ala Ser Ser Ala Glu Arg Thr Phe Leu Pro Asn
            20                  25                  30

Gly Asn Tyr Asn Ile Lys Ser Ile Phe Ser Gly Ser Leu Tyr Leu Ser
        35                  40                  45

Pro Val Ser Gly Ser Leu Thr Phe Ser Asn Glu Ser Ser Ala Asn Asn
    50                  55                  60

Gln Lys Trp Asn Val Glu Tyr Met Ala Glu Asn Arg Cys Phe Lys Ile
65                  70                  75                  80

Ser Asn Val Ala Glu Pro Asn Lys Tyr Leu Ser Tyr Asp Asn Phe Gly
                85                  90                  95

Phe Ile Ser Leu Asp Ser Leu Ser Asn Arg Cys Tyr Trp Phe Pro Ile
            100                 105                 110

Lys Ile Ala Val Asn Thr Tyr Ile Met Leu Ser Leu Asn Lys Val Asn
        115                 120                 125

Glu Leu Asp Tyr Ala Trp Asp Ile Tyr Asp Thr Asn Glu Asn Ile Leu
    130                 135                 140

Ser Gln Pro Leu Leu Leu Pro Asn Phe Asp Ile Tyr Asn Ser Asn
145                 150                 155                 160

Gln Met Phe Lys Leu Glu Lys Ile
                165

<210> SEQ ID NO 43
<211> LENGTH: 632
<212> TYPE: PRT
<213> ORGANISM: Artificial Sequence
<220> FEATURE:
<223> OTHER INFORMATION: Synthetic sequence, Strep-BHA3

<400> SEQUENCE: 43

Met Ala Ser Trp Ser His Pro Gln Phe Glu Lys Gly Ala Leu Glu Val
1               5                   10                  15

Leu Phe Gln Gly Pro Gly Tyr Gln Tyr Ser Asp Thr Ile Asp Leu Ala
            20                  25                  30

Asp Gly Asn Tyr Val Val Ser Arg Gly Asp Gly Trp Ile Leu Ser Arg
        35                  40                  45

Gln Asn Gln Ile Leu Gly Gly Ser Val Ile Ser Asn Gly Ser Thr Gly
    50                  55                  60

Ile Val Gly Asp Leu Arg Val Asn Asp Asn Ala Ile Pro Tyr Tyr Tyr
65                  70                  75                  80

Pro Thr Pro Ser Phe Asn Glu Glu Tyr Ile Lys Asn Asn Ile Gln Thr
                85                  90                  95

Val Phe Ala Asn Phe Thr Glu Ala Asn Gln Ile Pro Ile Gly Phe Glu

```
                100             105             110
Phe Ser Lys Thr Ala Pro Ser Asn Lys Asn Leu Tyr Met Tyr Leu Gln
            115             120             125
Tyr Thr Tyr Ile Arg Tyr Glu Ile Ile Lys Val Leu Gln His Glu Ile
            130             135             140
Ile Glu Arg Ala Val Leu Tyr Val Pro Ser Leu Gly Tyr Val Lys Ser
145             150             155             160
Ile Glu Phe Asn Pro Gly Glu Lys Ile Asn Lys Asp Phe Tyr Phe Leu
            165             170             175
Thr Asn Asp Lys Cys Ile Leu Asn Glu Gln Phe Leu Tyr Lys Lys Ile
            180             185             190
Leu Glu Thr Thr Lys Asn Ile Pro Thr Asn Asn Ile Phe Asn Ser Lys
            195             200             205
Val Ser Ser Thr Gln Arg Val Leu Pro Tyr Ser Asn Gly Leu Tyr Val
            210             215             220
Ile Asn Lys Gly Asp Gly Tyr Ile Arg Thr Asn Asp Lys Asp Leu Ile
225             230             235             240
Gly Thr Leu Leu Ile Glu Ala Gly Ser Ser Gly Ser Ile Ile Gln Pro
            245             250             255
Arg Leu Arg Asn Thr Thr Arg Pro Leu Phe Thr Thr Ser Asn Asp Ala
            260             265             270
Lys Phe Ser Gln Gln Tyr Thr Glu Glu Arg Leu Lys Asp Ala Phe Asn
            275             280             285
Val Gln Leu Phe Asn Thr Ser Thr Ser Leu Phe Lys Phe Val Glu Glu
            290             295             300
Ala Pro Ser Asn Lys Asn Ile Cys Ile Lys Ala Tyr Asn Thr Tyr Glu
305             310             315             320
Lys Tyr Glu Leu Ile Asp Tyr Gln Asn Gly Ser Ile Val Asn Lys Ala
            325             330             335
Glu Tyr Tyr Leu Pro Ser Leu Gly Tyr Cys Glu Val Thr Asn Ala Pro
            340             345             350
Ser Pro Glu Ser Glu Val Val Lys Thr Gln Val Ala Glu Asp Gly Phe
            355             360             365
Ile Gln Asn Gly Pro Glu Glu Glu Ile Val Val Gly Val Ile Asp Pro
            370             375             380
Ser Glu Asn Ile Gln Glu Ile Asn Thr Ala Ile Ser Asp Asn Tyr Thr
385             390             395             400
Tyr Asn Ile Pro Gly Ile Val Asn Asn Pro Phe Tyr Ile Leu Phe
            405             410             415
Thr Val Asn Thr Thr Gly Ile Tyr Lys Ile Asn Ala Gln Asn Asn Leu
            420             425             430
Pro Ser Leu Lys Ile Tyr Glu Ala Ile Gly Ser Gly Asn Arg Asn Phe
            435             440             445
Gln Ser Gly Asn Leu Cys Asp Asp Ile Lys Ala Ile Asn Tyr Ile
450             455             460
Thr Gly Phe Asp Ser Pro Asn Ala Lys Ser Tyr Leu Val Val Leu Leu
465             470             475             480
Asn Lys Asp Lys Asn Tyr Tyr Ile Arg Val Pro Gln Thr Ser Ser Asn
            485             490             495
Ile Glu Asn Gln Ile Lys Phe Lys Arg Glu Glu Gly Asp Leu Arg Asn
            500             505             510
Leu Met Asn Ser Ser Val Asn Ile Ile Asp Asn Leu Asn Ser Thr Gly
            515             520             525
```

```
Ala His Tyr Tyr Thr Arg Gln Ser Pro Asp Val His Asp Tyr Ile Ser
        530                 535                 540

Tyr Glu Phe Thr Ile Pro Gly Asn Phe Asn Asn Lys Asp Thr Ser Asn
545                 550                 555                 560

Ile Arg Leu Tyr Thr Ser Tyr Asn Gln Gly Ile Gly Thr Leu Phe Arg
                565                 570                 575

Val Thr Glu Thr Ile Asp Gly Tyr Asn Leu Ile Asn Ile Gln Gln Asn
            580                 585                 590

Leu Asn Leu Leu Asn Ser Thr Lys Ser Ile Arg Leu Leu Asn Gly Ala
        595                 600                 605

Ile Tyr Ile Leu Lys Val Glu Val Thr Glu Leu Asn Asn Tyr Asn Ile
        610                 615                 620

Lys Leu His Ile Asp Ile Thr Asn
625                 630

<210> SEQ ID NO 44
<211> LENGTH: 624
<212> TYPE: PRT
<213> ORGANISM: Artificial Sequence
<220> FEATURE:
<223> OTHER INFORMATION: Synthetic sequence, BHA3-Strep

<400> SEQUENCE: 44

Met Ala Ser Tyr Ser Asp Thr Ile Asp Leu Ala Asp Gly Asn Tyr Val
1               5                   10                  15

Val Ser Arg Gly Asp Gly Trp Ile Leu Ser Arg Gln Asn Gln Ile Leu
            20                  25                  30

Gly Gly Ser Val Ile Ser Asn Gly Ser Thr Gly Ile Val Gly Asp Leu
        35                  40                  45

Arg Val Asn Asp Asn Ala Ile Pro Tyr Tyr Pro Thr Pro Ser Phe
    50                  55                  60

Asn Glu Glu Tyr Ile Lys Asn Asn Ile Gln Thr Val Phe Ala Asn Phe
65                  70                  75                  80

Thr Glu Ala Asn Gln Ile Pro Ile Gly Phe Glu Phe Ser Lys Thr Ala
                85                  90                  95

Pro Ser Asn Lys Asn Leu Tyr Met Tyr Leu Gln Tyr Thr Tyr Ile Arg
            100                 105                 110

Tyr Glu Ile Ile Lys Val Leu Gln His Glu Ile Ile Glu Arg Ala Val
        115                 120                 125

Leu Tyr Val Pro Ser Leu Gly Tyr Val Lys Ser Ile Glu Phe Asn Pro
    130                 135                 140

Gly Glu Lys Ile Asn Lys Asp Phe Tyr Phe Leu Thr Asn Asp Lys Cys
145                 150                 155                 160

Ile Leu Asn Glu Gln Phe Leu Tyr Lys Lys Ile Leu Glu Thr Thr Lys
                165                 170                 175

Asn Ile Pro Thr Asn Asn Ile Phe Asn Ser Lys Val Ser Ser Thr Gln
            180                 185                 190

Arg Val Leu Pro Tyr Ser Asn Gly Leu Tyr Val Ile Asn Lys Gly Asp
        195                 200                 205

Gly Tyr Ile Arg Thr Asn Asp Lys Asp Leu Ile Gly Thr Leu Leu Ile
    210                 215                 220

Glu Ala Gly Ser Ser Gly Ser Ile Ile Gln Pro Arg Leu Arg Asn Thr
225                 230                 235                 240

Thr Arg Pro Leu Phe Thr Thr Ser Asn Asp Ala Lys Phe Ser Gln Gln
                245                 250                 255
```

Tyr Thr Glu Glu Arg Leu Lys Asp Ala Phe Asn Val Gln Leu Phe Asn
                260                 265                 270

Thr Ser Thr Ser Leu Phe Lys Phe Val Glu Glu Ala Pro Ser Asn Lys
            275                 280                 285

Asn Ile Cys Ile Lys Ala Tyr Asn Thr Tyr Glu Lys Tyr Glu Leu Ile
        290                 295                 300

Asp Tyr Gln Asn Gly Ser Ile Val Asn Lys Ala Glu Tyr Tyr Leu Pro
305                 310                 315                 320

Ser Leu Gly Tyr Cys Glu Val Thr Asn Ala Pro Ser Pro Glu Ser Glu
                325                 330                 335

Val Val Lys Thr Gln Val Ala Glu Asp Gly Phe Ile Gln Asn Gly Pro
            340                 345                 350

Glu Glu Glu Ile Val Val Gly Val Ile Asp Pro Ser Glu Asn Ile Gln
        355                 360                 365

Glu Ile Asn Thr Ala Ile Ser Asp Asn Tyr Thr Tyr Asn Ile Pro Gly
370                 375                 380

Ile Val Asn Asn Asn Pro Phe Tyr Ile Leu Phe Thr Val Asn Thr Thr
385                 390                 395                 400

Gly Ile Tyr Lys Ile Asn Ala Gln Asn Asn Leu Pro Ser Leu Lys Ile
                405                 410                 415

Tyr Glu Ala Ile Gly Ser Gly Asn Arg Asn Phe Gln Ser Gly Asn Leu
            420                 425                 430

Cys Asp Asp Asp Ile Lys Ala Ile Asn Tyr Ile Thr Gly Phe Asp Ser
        435                 440                 445

Pro Asn Ala Lys Ser Tyr Leu Val Val Leu Leu Asn Lys Asp Lys Asn
    450                 455                 460

Tyr Tyr Ile Arg Val Pro Gln Thr Ser Ser Asn Ile Glu Asn Gln Ile
465                 470                 475                 480

Lys Phe Lys Arg Glu Glu Gly Asp Leu Arg Asn Leu Met Asn Ser Ser
                485                 490                 495

Val Asn Ile Ile Asp Asn Leu Asn Ser Thr Gly Ala His Tyr Tyr Thr
            500                 505                 510

Arg Gln Ser Pro Asp Val His Asp Tyr Ile Ser Tyr Glu Phe Thr Ile
        515                 520                 525

Pro Gly Asn Phe Asn Asn Lys Asp Thr Ser Asn Ile Arg Leu Tyr Thr
    530                 535                 540

Ser Tyr Asn Gln Gly Ile Gly Thr Leu Phe Arg Val Thr Glu Thr Ile
545                 550                 555                 560

Asp Gly Tyr Asn Leu Ile Asn Ile Gln Gln Asn Leu Asn Leu Leu Asn
                565                 570                 575

Ser Thr Lys Ser Ile Arg Leu Leu Asn Gly Ala Ile Tyr Ile Leu Lys
            580                 585                 590

Val Glu Val Thr Glu Leu Asn Asn Tyr Asn Ile Lys Leu His Ile Asp
        595                 600                 605

Ile Thr Asn Gly Ser Gly Ser Ala Trp Ser His Pro Gln Phe Glu Lys
    610                 615                 620

<210> SEQ ID NO 45
<211> LENGTH: 778
<212> TYPE: PRT
<213> ORGANISM: Artificial Sequence
<220> FEATURE:
<223> OTHER INFORMATION: Synthetic sequence, linked-FL-HA(2+3)/B

<400> SEQUENCE: 45

```
Met Ala Ser Tyr Ser Asp Thr Ile Asp Leu Ala Asp Gly Asn Tyr Val
1               5                   10                  15

Val Ser Arg Gly Asp Gly Trp Ile Leu Ser Arg Gln Asn Gln Ile Leu
            20                  25                  30

Gly Gly Ser Val Ile Ser Asn Gly Ser Thr Gly Ile Val Gly Asp Leu
                35                  40                  45

Arg Val Asn Asp Asn Ala Ile Pro Tyr Tyr Pro Thr Pro Ser Phe
    50                  55                  60

Asn Glu Glu Tyr Ile Lys Asn Asn Ile Gln Thr Val Phe Ala Asn Phe
65                  70                  75                  80

Thr Glu Ala Asn Gln Ile Pro Ile Gly Phe Glu Phe Ser Lys Thr Ala
                85                  90                  95

Pro Ser Asn Lys Asn Leu Tyr Met Tyr Leu Gln Tyr Thr Tyr Ile Arg
                100                 105                 110

Tyr Glu Ile Ile Lys Val Leu Gln His Glu Ile Ile Glu Arg Ala Val
                115                 120                 125

Leu Tyr Val Pro Ser Leu Gly Tyr Val Lys Ser Ile Glu Phe Asn Pro
    130                 135                 140

Gly Glu Lys Ile Asn Lys Asp Phe Tyr Phe Leu Thr Asn Asp Lys Cys
145                 150                 155                 160

Ile Leu Asn Glu Gln Phe Leu Tyr Lys Lys Ile Leu Glu Thr Thr Lys
                165                 170                 175

Asn Ile Pro Thr Asn Asn Ile Phe Asn Ser Lys Val Ser Ser Thr Gln
                180                 185                 190

Arg Val Leu Pro Tyr Ser Asn Gly Leu Tyr Val Ile Asn Lys Gly Asp
            195                 200                 205

Gly Tyr Ile Arg Thr Asn Asp Lys Asp Leu Ile Gly Thr Leu Leu Ile
            210                 215                 220

Glu Ala Gly Ser Ser Gly Ser Ile Ile Gln Pro Arg Leu Arg Asn Thr
225                 230                 235                 240

Thr Arg Pro Leu Phe Thr Thr Ser Asn Asp Ala Lys Phe Ser Gln Gln
                245                 250                 255

Tyr Thr Glu Glu Arg Leu Lys Asp Ala Phe Asn Val Gln Leu Phe Asn
                260                 265                 270

Thr Ser Thr Ser Leu Phe Lys Phe Val Glu Glu Ala Pro Ser Asn Lys
                275                 280                 285

Asn Ile Cys Ile Lys Ala Tyr Asn Thr Tyr Glu Lys Tyr Glu Leu Ile
                290                 295                 300

Asp Tyr Gln Asn Gly Ser Ile Val Asn Lys Ala Glu Tyr Tyr Leu Pro
305                 310                 315                 320

Ser Leu Gly Tyr Cys Glu Val Thr Asn Ala Pro Ser Pro Glu Ser Glu
                325                 330                 335

Val Val Lys Thr Gln Val Ala Glu Asp Gly Phe Ile Gln Asn Gly Pro
                340                 345                 350

Glu Glu Glu Ile Val Val Gly Val Ile Asp Pro Ser Glu Asn Ile Gln
                355                 360                 365

Glu Ile Asn Thr Ala Ile Ser Asp Asn Tyr Thr Tyr Asn Ile Pro Gly
                370                 375                 380

Ile Val Asn Asn Asn Pro Phe Tyr Ile Leu Phe Thr Val Asn Thr Thr
385                 390                 395                 400

Gly Ile Tyr Lys Ile Asn Ala Gln Asn Asn Leu Pro Ser Leu Lys Ile
                405                 410                 415
```

-continued

```
Tyr Glu Ala Ile Gly Ser Gly Asn Arg Asn Phe Gln Ser Gly Asn Leu
            420             425             430

Cys Asp Asp Ile Lys Ala Ile Asn Tyr Ile Thr Gly Phe Asp Ser
        435             440             445

Pro Asn Ala Lys Ser Tyr Leu Val Val Leu Asn Lys Asp Lys Asn
    450             455             460

Tyr Tyr Ile Arg Val Pro Gln Thr Ser Ser Asn Ile Glu Asn Gln Ile
465             470             475             480

Lys Phe Lys Arg Glu Glu Gly Asp Leu Arg Asn Leu Met Asn Ser Ser
            485             490             495

Val Asn Ile Ile Asp Asn Leu Asn Ser Thr Gly Ala His Tyr Tyr Thr
            500             505             510

Arg Gln Ser Pro Asp Val His Asp Tyr Ile Ser Tyr Glu Phe Thr Ile
    515             520             525

Pro Gly Asn Phe Asn Asn Lys Asp Thr Ser Asn Ile Arg Leu Tyr Thr
    530             535             540

Ser Tyr Asn Gln Gly Ile Gly Thr Leu Phe Arg Val Thr Glu Thr Ile
545             550             555             560

Asp Gly Tyr Asn Leu Ile Asn Ile Gln Gln Asn Leu Asn Leu Leu Asn
            565             570             575

Ser Thr Lys Ser Ile Arg Leu Leu Asn Gly Ala Ile Tyr Ile Leu Lys
            580             585             590

Val Glu Val Thr Glu Leu Asn Asn Tyr Asn Ile Lys Leu His Ile Asp
            595             600             605

Ile Thr Asn Gly Ser Gly Gly Asp Asp Pro Gly Ser Ala Glu Arg
    610             615             620

Thr Phe Leu Pro Asn Gly Asn Tyr Asn Ile Lys Ser Ile Phe Ser Gly
625             630             635             640

Ser Leu Tyr Leu Ser Pro Val Ser Gly Ser Leu Thr Phe Ser Asn Glu
            645             650             655

Ser Ser Ala Asn Asn Gln Lys Trp Asn Val Glu Tyr Met Ala Glu Asn
            660             665             670

Arg Cys Phe Lys Ile Ser Asn Val Ala Glu Pro Asn Lys Tyr Leu Ser
            675             680             685

Tyr Asp Asn Phe Gly Phe Ile Ser Leu Asp Ser Leu Ser Asn Arg Cys
    690             695             700

Tyr Trp Phe Pro Ile Lys Ile Ala Val Asn Thr Tyr Ile Met Leu Ser
705             710             715             720

Leu Asn Lys Val Asn Glu Leu Asp Tyr Ala Trp Asp Ile Tyr Asp Thr
            725             730             735

Asn Glu Asn Ile Leu Ser Gln Pro Leu Leu Leu Pro Asn Phe Asp
            740             745             750

Ile Tyr Asn Ser Asn Gln Met Phe Lys Leu Glu Lys Ile Gly Ser Gly
    755             760             765

Ser Ala Trp Ser His Pro Gln Phe Glu Lys
    770             775
```

<210> SEQ ID NO 46
<211> LENGTH: 263
<212> TYPE: PRT
<213> ORGANISM: Artificial Sequence
<220> FEATURE:
<223> OTHER INFORMATION: Synthetic sequence, BHA3mini-Strep

<400> SEQUENCE: 46

```
Met Ala Ser Glu Asn Ile Gln Glu Ile Asn Thr Ala Ile Ser Asp Asn
1               5                   10                  15

Tyr Thr Tyr Asn Ile Pro Gly Ile Val Asn Asn Asn Pro Phe Tyr Ile
                20                  25                  30

Leu Phe Thr Val Asn Thr Thr Gly Ile Tyr Lys Ile Asn Ala Gln Asn
            35                  40                  45

Asn Leu Pro Ser Leu Lys Ile Tyr Glu Ala Ile Gly Ser Gly Asn Arg
        50                  55                  60

Asn Phe Gln Ser Gly Asn Leu Cys Asp Asp Asp Ile Lys Ala Ile Asn
65                  70                  75                  80

Tyr Ile Thr Gly Phe Asp Ser Pro Asn Ala Lys Ser Tyr Leu Val Val
                85                  90                  95

Leu Leu Asn Lys Asp Lys Asn Tyr Tyr Ile Arg Val Pro Gln Thr Ser
            100                 105                 110

Ser Asn Ile Glu Asn Gln Ile Lys Phe Lys Arg Glu Glu Gly Asp Leu
        115                 120                 125

Arg Asn Leu Met Asn Ser Ser Val Asn Ile Ile Asp Asn Leu Asn Ser
            130                 135                 140

Thr Gly Ala His Tyr Tyr Thr Arg Gln Ser Pro Asp Val His Asp Tyr
145                 150                 155                 160

Ile Ser Tyr Glu Phe Thr Ile Pro Gly Asn Phe Asn Asn Lys Asp Thr
                165                 170                 175

Ser Asn Ile Arg Leu Tyr Thr Ser Tyr Asn Gln Gly Ile Gly Thr Leu
            180                 185                 190

Phe Arg Val Thr Glu Thr Ile Asp Gly Tyr Asn Leu Ile Asn Ile Gln
        195                 200                 205

Gln Asn Leu Asn Leu Leu Asn Ser Thr Lys Ser Ile Arg Leu Leu Asn
    210                 215                 220

Gly Ala Ile Tyr Ile Leu Lys Val Glu Val Thr Glu Leu Asn Asn Tyr
225                 230                 235                 240

Asn Ile Lys Leu His Ile Asp Ile Thr Asn Gly Ser Gly Ser Ala Trp
                245                 250                 255

Ser His Pro Gln Phe Glu Lys
            260

<210> SEQ ID NO 47
<211> LENGTH: 417
<212> TYPE: PRT
<213> ORGANISM: Artificial Sequence
<220> FEATURE:
<223> OTHER INFORMATION: Synthetic sequence, linked-mini-HA(2+3)/B

<400> SEQUENCE: 47

Met Ala Ser Glu Asn Ile Gln Glu Ile Asn Thr Ala Ile Ser Asp Asn
1               5                   10                  15

Tyr Thr Tyr Asn Ile Pro Gly Ile Val Asn Asn Asn Pro Phe Tyr Ile
                20                  25                  30

Leu Phe Thr Val Asn Thr Thr Gly Ile Tyr Lys Ile Asn Ala Gln Asn
            35                  40                  45

Asn Leu Pro Ser Leu Lys Ile Tyr Glu Ala Ile Gly Ser Gly Asn Arg
        50                  55                  60

Asn Phe Gln Ser Gly Asn Leu Cys Asp Asp Asp Ile Lys Ala Ile Asn
65                  70                  75                  80

Tyr Ile Thr Gly Phe Asp Ser Pro Asn Ala Lys Ser Tyr Leu Val Val
                85                  90                  95
```

```
Leu Leu Asn Lys Asp Lys Asn Tyr Tyr Ile Arg Val Pro Gln Thr Ser
            100                 105                 110

Ser Asn Ile Glu Asn Gln Ile Lys Phe Lys Arg Glu Glu Gly Asp Leu
        115                 120                 125

Arg Asn Leu Met Asn Ser Ser Val Asn Ile Ile Asp Asn Leu Asn Ser
    130                 135                 140

Thr Gly Ala His Tyr Tyr Thr Arg Gln Ser Pro Asp Val His Asp Tyr
145                 150                 155                 160

Ile Ser Tyr Glu Phe Thr Ile Pro Gly Asn Phe Asn Asn Lys Asp Thr
                165                 170                 175

Ser Asn Ile Arg Leu Tyr Thr Ser Tyr Asn Gln Gly Ile Gly Thr Leu
            180                 185                 190

Phe Arg Val Thr Glu Thr Ile Asp Gly Tyr Asn Leu Ile Asn Ile Gln
        195                 200                 205

Gln Asn Leu Asn Leu Leu Asn Ser Thr Lys Ser Ile Arg Leu Leu Asn
    210                 215                 220

Gly Ala Ile Tyr Ile Leu Lys Val Glu Val Thr Glu Leu Asn Asn Tyr
225                 230                 235                 240

Asn Ile Lys Leu His Ile Asp Ile Thr Asn Gly Ser Gly Gly Asp Asp
                245                 250                 255

Pro Pro Gly Ser Ala Glu Arg Thr Phe Leu Pro Asn Gly Asn Tyr Asn
            260                 265                 270

Ile Lys Ser Ile Phe Ser Gly Ser Leu Tyr Leu Ser Pro Val Ser Gly
        275                 280                 285

Ser Leu Thr Phe Ser Asn Glu Ser Ser Ala Asn Asn Gln Lys Trp Asn
    290                 295                 300

Val Glu Tyr Met Ala Glu Asn Arg Cys Phe Lys Ile Ser Asn Val Ala
305                 310                 315                 320

Glu Pro Asn Lys Tyr Leu Ser Tyr Asp Asn Phe Gly Phe Ile Ser Leu
                325                 330                 335

Asp Ser Leu Ser Asn Arg Cys Tyr Trp Phe Pro Ile Lys Ile Ala Val
            340                 345                 350

Asn Thr Tyr Ile Met Leu Ser Leu Asn Lys Val Asn Glu Leu Asp Tyr
        355                 360                 365

Ala Trp Asp Ile Tyr Asp Thr Asn Glu Asn Ile Leu Ser Gln Pro Leu
370                 375                 380

Leu Leu Leu Pro Asn Phe Asp Ile Tyr Asn Ser Asn Gln Met Phe Lys
                385                 390                 395                 400

Leu Glu Lys Ile Gly Ser Gly Ser Ala Trp Ser His Pro Gln Phe Glu
            405                 410                 415

Lys

<210> SEQ ID NO 48
<211> LENGTH: 417
<212> TYPE: PRT
<213> ORGANISM: Artificial Sequence
<220> FEATURE:
<223> OTHER INFORMATION: Synthetic sequence, linked-mini-HA(2+3)/CB

<400> SEQUENCE: 48

Met Ala Ser Glu Asn Ile Gln Glu Ile Asn Thr Ala Ile Ser Asp Asn
1               5                   10                  15

Tyr Thr Tyr Asn Ile Pro Gly Ile Val Asn Asn Pro Phe Tyr Ile
            20                  25                  30

Leu Phe Thr Val Asn Thr Thr Gly Ile Tyr Lys Ile Asn Ala Gln Asn
```

```
                35                  40                  45
Asn Leu Pro Ser Leu Lys Ile Tyr Glu Ala Ile Gly Ser Gly Asn Arg
 50                  55                  60
Asn Phe Gln Ser Gly Asn Leu Cys Asp Asp Ile Lys Ala Ile Asn
 65                  70                  75                  80
Tyr Ile Thr Gly Phe Asp Ser Pro Asn Ala Lys Ser Tyr Leu Val Val
                 85                  90                  95
Leu Leu Asn Lys Asp Lys Asn Tyr Tyr Ile Arg Val Pro Gln Thr Ser
                100                 105                 110
Ser Asn Ile Glu Asn Gln Ile Lys Phe Lys Arg Glu Glu Gly Asp Leu
                115                 120                 125
Arg Asn Leu Met Asn Ser Ser Val Asn Ile Ile Asp Asn Leu Asn Ser
130                 135                 140
Thr Gly Ala His Tyr Tyr Thr Arg Gln Ser Pro Asp Val His Asp Tyr
145                 150                 155                 160
Ile Ser Tyr Glu Phe Thr Ile Pro Gly Asn Phe Asn Asn Lys Asp Thr
                165                 170                 175
Ser Asn Ile Arg Leu Tyr Thr Ser Tyr Asn Gln Gly Ile Gly Thr Leu
                180                 185                 190
Phe Arg Val Thr Glu Thr Ile Asp Gly Tyr Asn Leu Ile Asn Ile Gln
                195                 200                 205
Gln Asn Leu Asn Leu Leu Asn Ser Thr Lys Ser Ile Arg Leu Leu Asn
210                 215                 220
Gly Ala Ile Tyr Ile Leu Lys Val Glu Val Thr Glu Leu Asn Asn Tyr
225                 230                 235                 240
Asn Ile Lys Leu His Ile Asp Ile Thr Asn Gly Ser Gly Gly Asp Asp
                245                 250                 255
Pro Pro Gly Ser Ser Glu Arg Thr Phe Leu Pro Asn Gly Asn Tyr Lys
                260                 265                 270
Ile Lys Ser Leu Phe Ser Asp Ser Leu Tyr Leu Thr Tyr Ser Ser Gly
                275                 280                 285
Ala Leu Ser Phe Ser Asn Thr Ser Ser Leu Asp Asn Gln Lys Trp Lys
290                 295                 300
Leu Glu Tyr Ile Ser Ser Ser Asn Gly Phe Arg Phe Ser Asn Val Ala
305                 310                 315                 320
Glu Pro Asn Lys Tyr Leu Ala Tyr Asn Asp Tyr Gly Phe Ile Tyr Leu
                325                 330                 335
Ser Ser Ser Ser Asn Asn Ser Leu Trp Asn Pro Ile Lys Ile Ala Ile
                340                 345                 350
Asn Ser Tyr Ile Ile Cys Thr Leu Ser Ile Val Asn Val Thr Asp Tyr
                355                 360                 365
Ala Trp Thr Ile Tyr Asp Asn Asn Asn Ile Thr Asp Gln Pro Ile
370                 375                 380
Leu Asn Leu Pro Asn Phe Asp Ile Asn Ser Asn Gln Ile Leu Lys
385                 390                 395                 400
Leu Glu Lys Leu Gly Ser Gly Ser Ala Trp Ser His Pro Gln Phe Glu
                405                 410                 415
Lys

<210> SEQ ID NO 49
<211> LENGTH: 417
<212> TYPE: PRT
<213> ORGANISM: Artificial Sequence
<220> FEATURE:
```

<223> OTHER INFORMATION: Synthetic sequence, linked-mini-HA(2+3)/CB-YFDY

<400> SEQUENCE: 49

```

Leu Glu Lys Leu Gly Ser Gly Ser Ala Trp Ser His Pro Gln Phe Glu
                405                 410                 415

Lys

<210> SEQ ID NO 50
<211> LENGTH: 417
<212> TYPE: PRT
<213> ORGANISM: Artificial Sequence
<220> FEATURE:
<223> OTHER INFORMATION: Synthetic sequence, linked-mini-HA(2+3)/CB-LD-
      YFDY

<400> SEQUENCE: 50

Met Ala Ser Glu Asn Ile Gln Glu Ile Asn Thr Ala Ile Ser Asp Asn
1               5                   10                  15

Tyr Thr Tyr Asn Ile Pro Gly Ile Val Asn Asn Asn Pro Phe Tyr Ile
                20                  25                  30

Leu Phe Thr Val Asn Thr Thr Gly Ile Tyr Lys Ile Asn Ala Gln Asn
            35                  40                  45

Asn Leu Pro Ser Leu Lys Ile Tyr Glu Ala Ile Gly Ser Gly Asn Arg
    50                  55                  60

Asn Phe Gln Ser Gly Asn Leu Cys Asp Asp Ile Lys Ala Ile Asn
65                  70                  75                  80

Tyr Ile Thr Gly Phe Asp Ser Pro Asn Ala Lys Ser Tyr Leu Val Val
                85                  90                  95

Leu Leu Asn Lys Asp Lys Asn Tyr Tyr Ile Arg Val Pro Gln Thr Ser
            100                 105                 110

Ser Asn Ile Glu Asn Gln Ile Lys Phe Lys Arg Glu Gly Asp Leu
    115                 120                 125

Arg Asn Leu Met Asn Ser Ser Val Asn Ile Ile Asp Asn Leu Asn Ser
130                 135                 140

Thr Gly Ala His Tyr Tyr Thr Arg Gln Ser Pro Asp Val His Asp Tyr
145                 150                 155                 160

Ile Ser Tyr Glu Phe Thr Ile Pro Gly Asn Phe Asn Asn Lys Asp Thr
                165                 170                 175

Ser Asn Ile Arg Leu Tyr Thr Ser Tyr Asn Gln Gly Ile Gly Thr Leu
            180                 185                 190

Phe Arg Val Thr Glu Thr Ile Asp Gly Tyr Asn Leu Ile Asn Ile Gln
        195                 200                 205

Gln Asn Leu Asn Leu Leu Asn Ser Thr Lys Ser Ile Arg Leu Leu Asn
    210                 215                 220

Gly Ala Ile Tyr Ile Leu Lys Val Glu Val Thr Glu Leu Asn Asn Tyr
225                 230                 235                 240

Asn Ile Lys Leu His Ile Asp Ile Thr Asn Gly Ser Gly Gly Asp Asp
                245                 250                 255

Pro Pro Gly Ser Ser Glu Arg Thr Phe Leu Pro Asn Gly Asn Tyr Lys
            260                 265                 270

Ile Lys Ser Leu Phe Ser Asp Ser Leu Tyr Leu Thr Tyr Ser Ser Gly
        275                 280                 285

Ala Leu Ser Phe Ser Asn Thr Ser Ser Asp Asn Gln Lys Trp Lys
    290                 295                 300

Leu Glu Tyr Ile Ser Ser Ser Asn Gly Phe Arg Phe Ser Asn Val Ala
305                 310                 315                 320

Glu Pro Asn Lys Tyr Leu Ala Tyr Asn Asp Asp Gly Tyr Ile Tyr Leu
                325                 330                 335

```
Ser Ser Ser Ser Asn Asn Ser Leu Trp Asn Pro Ile Lys Ile Ala Ile
            340             345                 350

Asn Ser Tyr Ile Ile Cys Thr Leu Ser Ile Val Asn Val Thr Asp Tyr
        355                 360                 365

Ala Trp Thr Ile Tyr Asp Asn Asn Asn Ile Thr Asp Gln Pro Ile
370                 375                 380

Leu Asn Leu Pro Asn Phe Asp Ile Asn Asn Ser Asn Gln Ile Leu Lys
385             390                 395                 400

Leu Glu Lys Leu Gly Ser Gly Ser Ala Trp Ser His Pro Gln Phe Glu
                405                 410                 415

Lys

<210> SEQ ID NO 51
<211> LENGTH: 417
<212> TYPE: PRT
<213> ORGANISM: Artificial Sequence
<220> FEATURE:
<223> OTHER INFORMATION: Synthetic sequence, linked-mini-HA(2+3)/CB-IC

<400> SEQUENCE: 51

Met Ala Ser Glu Asn Ile Gln Glu Ile Asn Thr Ala Ile Ser Asp Asn
1               5                   10                  15

Tyr Thr Tyr Asn Ile Pro Gly Ile Val Asn Asn Pro Phe Tyr Ile
                20                  25                  30

Leu Phe Thr Val Asn Thr Thr Gly Ile Tyr Lys Ile Asn Ala Gln Asn
            35                  40                  45

Asn Leu Pro Ser Leu Lys Ile Tyr Glu Ala Ile Gly Ser Gly Asn Arg
50                  55                  60

Asn Phe Gln Ser Gly Asn Leu Cys Asp Asp Ile Lys Ala Ile Asn
65                  70                  75                  80

Tyr Ile Thr Gly Phe Asp Ser Pro Asn Ala Lys Ser Tyr Leu Val Val
                85                  90                  95

Leu Leu Asn Lys Asp Lys Asn Tyr Tyr Ile Arg Val Pro Gln Thr Ser
            100                 105                 110

Ser Asn Ile Glu Asn Gln Ile Lys Phe Lys Arg Glu Glu Gly Asp Leu
        115                 120                 125

Arg Asn Leu Met Asn Ser Ser Val Asn Ile Ile Asp Asn Leu Asn Ser
130                 135                 140

Thr Gly Ala His Tyr Tyr Thr Arg Gln Ser Pro Asp Val His Asp Tyr
145                 150                 155                 160

Ile Ser Tyr Glu Phe Thr Ile Pro Gly Asn Phe Asn Asn Lys Asp Thr
                165                 170                 175

Ser Asn Ile Arg Leu Tyr Thr Ser Tyr Asn Gln Gly Ile Gly Thr Leu
            180                 185                 190

Phe Arg Val Thr Glu Thr Ile Asp Gly Tyr Asn Leu Ile Asn Ile Gln
        195                 200                 205

Gln Asn Leu Asn Leu Leu Asn Ser Thr Lys Ser Ile Arg Leu Leu Asn
210                 215                 220

Gly Ala Ile Tyr Ile Leu Lys Val Glu Val Thr Glu Leu Asn Asn Tyr
225                 230                 235                 240

Asn Ile Lys Leu His Ile Asp Ile Thr Asn Gly Ser Gly Gly Asp Asp
                245                 250                 255

Pro Pro Gly Ser Ser Glu Arg Thr Phe Leu Pro Asn Gly Asn Tyr Lys
            260                 265                 270

Ile Lys Ser Leu Phe Ser Asp Ser Leu Tyr Leu Thr Tyr Ser Ser Gly
```

```
                275                 280                 285
Ala Leu Ser Phe Ser Asn Thr Ser Ser Leu Asp Asn Gln Lys Trp Lys
290                 295                 300

Leu Glu Tyr Ile Ser Ser Ser Asn Gly Phe Arg Phe Ser Asn Val Ala
305                 310                 315                 320

Glu Pro Asn Lys Tyr Leu Ala Tyr Asn Asp Tyr Gly Phe Ile Tyr Leu
                325                 330                 335

Ser Ser Ser Ser Asn Asn Ser Leu Trp Asn Pro Cys Lys Ile Ala Ile
                340                 345                 350

Asn Ser Tyr Ile Ile Cys Thr Leu Ser Ile Val Asn Val Thr Asp Tyr
                355                 360                 365

Ala Trp Thr Ile Tyr Asp Asn Asn Asn Ile Thr Asp Gln Pro Ile
                370                 375                 380

Leu Asn Leu Pro Asn Phe Asp Ile Asn Asn Ser Asn Gln Ile Leu Lys
385                 390                 395                 400

Leu Glu Lys Leu Gly Ser Gly Ser Ala Trp Ser His Pro Gln Phe Glu
                405                 410                 415

Lys

<210> SEQ ID NO 52
<211> LENGTH: 417
<212> TYPE: PRT
<213> ORGANISM: Artificial Sequence
<220> FEATURE:
<223> OTHER INFORMATION: Synthetic sequence, linked-mini-HA(2+3)/CB-ITCC

<400> SEQUENCE: 52

Met Ala Ser Glu Asn Ile Gln Glu Ile Asn Thr Ala Ile Ser Asp Asn
1               5                   10                  15

Tyr Thr Tyr Asn Ile Pro Gly Ile Val Asn Asn Pro Phe Tyr Ile
                20                  25                  30

-continued

```
Gly Ala Ile Tyr Ile Leu Lys Val Glu Val Thr Glu Leu Asn Asn Tyr
225                 230                 235                 240

Asn Ile Lys Leu His Ile Asp Ile Thr Asn Gly Ser Gly Gly Asp Asp
                245                 250                 255

Pro Pro Gly Ser Ser Glu Arg Thr Phe Leu Pro Asn Gly Asn Tyr Lys
            260                 265                 270

Ile Lys Ser Leu Phe Ser Asp Ser Leu Tyr Leu Thr Tyr Ser Ser Gly
            275                 280                 285

Ala Leu Ser Phe Ser Asn Thr Ser Ser Leu Asp Asn Gln Lys Trp Lys
        290                 295                 300

Leu Glu Tyr Ile Ser Ser Ser Asn Gly Phe Arg Phe Ser Asn Val Ala
305                 310                 315                 320

Glu Pro Asn Lys Tyr Leu Ala Tyr Asn Asp Tyr Gly Phe Ile Tyr Leu
                325                 330                 335

Ser Ser Ser Ser Asn Asn Ser Leu Trp Asn Pro Cys Lys Ile Ala Ile
            340                 345                 350

Asn Ser Tyr Ile Ile Cys Thr Leu Ser Ile Val Asn Val Thr Asp Tyr
        355                 360                 365

Ala Trp Thr Ile Tyr Asp Asn Asn Asn Ile Thr Asp Gln Pro Ile
    370                 375                 380

Leu Asn Leu Pro Asn Phe Asp Ile Asn Asn Ser Asn Gln Ile Leu Lys
385                 390                 395                 400

Leu Glu Lys Leu Gly Ser Gly Ser Ala Trp Ser His Pro Gln Phe Glu
                405                 410                 415

Lys
```